US011213602B2

(12) United States Patent
Song

(10) Patent No.: US 11,213,602 B2
(45) Date of Patent: Jan. 4, 2022

(54) MULTI-OIL DIFFUSER

(71) Applicant: PUZHEN LIFE CO., LIMITED, Shatin (HK)

(72) Inventor: Baoje Song, New York, NY (US)

(73) Assignee: PUZHEN LIFE CO., LIMITED, Hong Kong (HK)

( * ) Notice: Subject to any disclaimer, the term of this patent is extended or adjusted under 35 U.S.C. 154(b) by 0 days.

(21) Appl. No.: 16/895,611

(22) Filed: Jun. 8, 2020

(65) Prior Publication Data

US 2021/0015956 A1 Jan. 21, 2021

Related U.S. Application Data

(63) Continuation-in-part of application No. 16/863,663, filed on Apr. 30, 2020, now Pat. No. 11,000,618, which is a continuation-in-part of application No. 16/033,037, filed on Jul. 11, 2018, and a continuation-in-part of application No. 16/526,500, filed on Jul. 30, 2019, said application No. 16/033,037 is a continuation-in-part of application No. PCT/CN2018/081092, filed on Mar. 29, 2018, and a continuation-in-part of application No. PCT/CN2018/081091, filed on Mar. 29, 2018.

(60) Provisional application No. 62/755,099, filed on Nov. 2, 2018.

(51) Int. Cl.
*A61L 9/14* (2006.01)

(52) U.S. Cl.
CPC .......... *A61L 9/14* (2013.01); *A61L 2209/133* (2013.01); *A61L 2209/134* (2013.01)

(58) Field of Classification Search
CPC . A61L 9/14; A61L 2209/133; A61L 2209/134
See application file for complete search history.

(56) References Cited

U.S. PATENT DOCUMENTS

| | | | |
|---|---|---|---|
| 3,866,414 | A | 2/1975 | Bahr |
| 4,184,615 | A | 1/1980 | Wright |
| 4,550,706 | A | 11/1985 | Hoffman |
| 4,974,573 | A | 12/1990 | Jensen |
| 7,878,418 | B2 | 2/2011 | Sevy |
| 8,857,735 | B2 | 10/2014 | Rosener et al. |

(Continued)

FOREIGN PATENT DOCUMENTS

| | | | |
|---|---|---|---|
| CN | 2751868 | Y | 1/2006 |
| CN | 201832737 | U | 5/2011 |

(Continued)

OTHER PUBLICATIONS

European Search Report dated Sep. 21, 2021 as received in EP Application No. 21178259.4.

(Continued)

*Primary Examiner* — Sean E Conley
(74) *Attorney, Agent, or Firm* — Dorsey & Whitney LLP

(57) ABSTRACT

An essential oil reflux-type atomizer comprising the following structures: a chassis, housing, atomization chamber, gas pump, gas tube, gas nozzle, oil nozzle, and filter atomization mechanism. Oil and gas flow together at the gas and oil nozzles to disperse and atomize the oil in the gas flow. A heater is used to raise the temperature of the oil where it is atomized, either by heating the oil itself or by heating the gas flowing into the oil. Thus, the atomizer can have improved performance, especially with essential oils having high viscosity and molecular weight.

20 Claims, 16 Drawing Sheets

(56) References Cited

U.S. PATENT DOCUMENTS

| | | | | |
|---|---|---|---|---|
| 9,211,357 | B1 | 12/2015 | Li | |
| 9,358,557 | B2 | 6/2016 | Young et al. | |
| 9,415,130 | B2 | 8/2016 | Sevy | |
| 9,421,295 | B1 * | 8/2016 | Li | A61L 9/125 |
| 2002/0068023 | A1 | 6/2002 | Davis | |
| 2003/0132311 | A1 | 7/2003 | Dorendorf et al. | |
| 2005/0116059 | A1 | 6/2005 | Lin | |
| 2006/0145368 | A1 | 7/2006 | Thomas | |
| 2007/0163577 | A1 | 7/2007 | Van | |
| 2007/0242464 | A1 | 10/2007 | Yu et al. | |
| 2008/0121660 | A1 | 5/2008 | Ophardt | |
| 2011/0259974 | A1 | 10/2011 | Cooper et al. | |
| 2016/0000959 | A1 | 1/2016 | Sevy | |
| 2016/0361678 | A1 * | 12/2016 | Blackley | G01N 33/0011 |
| 2017/0246336 | A1 * | 8/2017 | Suissa | B05B 7/0081 |
| 2019/0299230 | A1 | 10/2019 | Song | |
| 2020/0016344 | A1 * | 1/2020 | Scheck | A61M 15/009 |
| 2020/0022411 | A1 | 1/2020 | Krietzman | |
| 2020/0139387 | A1 | 5/2020 | Song | |

FOREIGN PATENT DOCUMENTS

| | | | |
|---|---|---|---|
| CN | 202184967 | U | 4/2012 |
| CN | 202741276 | U | 2/2013 |
| CN | 103041480 | A | 4/2013 |
| CN | 103230638 | A | 8/2013 |
| CN | 103375230 | A | 10/2013 |
| CN | 203436642 | U | 2/2014 |
| CN | 203916959 | U | 11/2014 |
| CN | 204072864 | U | 1/2015 |
| CN | 204072868 | U | 1/2015 |
| CN | 204396240 | U | 6/2015 |
| CN | 105013059 | A | 11/2015 |
| CN | 107758798 | A | 3/2016 |
| CN | 105536021 | A | 5/2016 |
| CN | 105561367 | A | 5/2016 |
| CN | 106423613 | A | 2/2017 |
| CN | 205966339 | U | 2/2017 |
| CN | 206046319 | U | 3/2017 |
| TW | 411243 | S | 11/2000 |
| WO | 2013030117 | A2 | 3/2013 |

OTHER PUBLICATIONS

European Search Report dated Sep. 20, 2021 as received in EP Application No. 21171675.8.

* cited by examiner

MULTI-OIL DIFFUSER

CROSS-REFERENCE TO RELATED APPLICATIONS

The present disclosure is a continuation-in-part of U.S. patent application Ser. No. 16/863,663, filed 30 Apr. 2020, now U.S. Pat. No. 11,000,618. U.S. patent application Ser. No. 16/863,663 is a continuation-in-part of U.S. patent application Ser. No. 16/033,037, filed 11 Jul. 2018, now U.S. Pat. No. 11,123,757, and U.S. patent application Ser. No. 16/526,500, filed 30 Jul. 2019. U.S. patent application Ser. No. 16/033,037 is a continuation-in-part of PCT/CN2018/081092, filed 29 Mar. 2018, and PCT/CN2018/081091, filed 29 Mar. 2018. U.S. patent application Ser. No. 16/526,500 claims priority to U.S. Provisional Patent Application No. 62/755,099, filed 2 Nov. 2018. The contents of the entire above-mentioned patent applications are hereby incorporated by reference.

TECHNICAL FIELD

The present disclosure relates to the field of atomizers, and more particularly to an airflow guided essential oil reflux-type atomizer.

BACKGROUND

In daily life, essential oils are often used to improve the surrounding environment or to perform medical treatment, such as sterilization, disinfection or changing environmental odor, etc. When using the essential oils, an atomizer is often used to atomize the essential oils for facilitating diffusion of the essential oils into the environment.

SUMMARY

One aspect of the present disclosure relates to an essential oil atomizer. The atomizer can comprise a housing configured to connect to an oil receptacle, with the housing having an atomization chamber from which atomized oil can be expelled, an atomizer nozzle assembly configured to expel atomized oil and gas into the atomization chamber, wherein the atomizer nozzle assembly is configured to be in fluid communication with oil in the oil receptacle, and a heater connected to the housing and configured to apply heat to the oil or gas.

In some embodiments, the atomizer nozzle assembly can comprise a gas nozzle and an oil nozzle, wherein the oil nozzle is configured to be in fluid communication with the oil receptacle and wherein the gas nozzle is configured to expel the gas across the oil nozzle.

The heater can be configured to heat oil in the atomizer nozzle assembly or in the oil receptacle. In some embodiments, the heater can be configured to be concentric with the oil receptacle. The heater can be configured to heat gas before or when the gas enters into the atomizer nozzle assembly. The heater can also be configured to apply heat to a gas line entering the atomizer nozzle assembly. The heater can be substantially cylindrical or can comprise a heating element and an insulator positioned radially external to the heating element.

Another aspect of the disclosure relates to an essential oil atomizer having a housing connectable to an oil receptacle, an atomizer having a nozzle assembly attached to the housing and configured to atomize oil from the oil receptacle by directing flow of a gas across the oil at the nozzle assembly, wherein the flow of the gas and atomized oil is configured to pass out of the housing, and a heater configured to raise a temperature of the oil at the nozzle assembly.

In some embodiments, the heater can be configured to raise the temperature of the nozzle assembly. The heater can be configured to raise the temperature of the oil by heating the gas before or while it flows through the nozzle assembly. The heater can be configured to heat the gas at a position external to the nozzle assembly. In some embodiments, the heater can be configured to raise the temperature of the oil by heating the oil before or while it flows to the nozzle assembly. The heater can be configured to heat the oil in the oil receptacle. In some embodiments, the heater can be configured to raise the temperature of the oil to be within a range of about 35 degrees Celsius to about 40 degrees Celsius.

Yet another aspect of the disclosure relates to a method of atomizing essential oil, wherein the method comprises generating gas flow through a gas nozzle, generating oil flow through an oil nozzle, wherein the gas flow passes over an outlet of the oil nozzle to atomize the oil flow, and raising a temperature of the oil flow to increase atomization of the oil flow as the gas flow passes over the outlet.

Raising the temperature of the oil flow can comprise applying heat to the gas flow and moving (e.g., driving or drawing) the oil flow into the gas flow, applying heat to an oil container from which the oil flows, or applying heat to the gas nozzle or the oil nozzle.

Another aspect of the present disclosure relates to an essential oil atomizer, comprising a housing and a first oil diffuser and a second oil diffuser located within the housing. Each of the first and second oil diffusers can comprise an oil receptacle configured to store oil, and an atomizer nozzle assembly configured to diffuse oil and gas. The essential oil atomizer can further comprise a heater configured to apply heat to the oil or gas.

In some embodiments, the essential oil atomizer comprises a first pump configured to provide gas to the first oil diffuser, and a second pump configured to provide gas to the second oil diffuser. The heater can comprise a first heating element configured to supply heat to the first oil diffuser, and a second heating element configured to supply heat to the second oil diffuser. The first heating element and the second heating element can be configured to heat the respective oil receptacles of the first and second oil diffusers. The first heating element and the second heating element are configured to heat the respective atomizer nozzle assemblies of the first and second oil diffusers.

In some embodiments, each atomizer nozzle assembly can comprise an oil nozzle and a gas nozzle, wherein the heater can configured to apply heat to at least one gas nozzle of the first and second oil diffusers. The heater can comprise a heating block positioned adjacent at least one of the atomizer nozzle assemblies. The heater can be configured to apply heat to a first gas line of the first oil diffuser and a second gas line of the second oil diffuser.

In some embodiments, the atomized oil and gas from the first and second oil diffuser is expelled into a mixing chamber to form a mixture of atomized oil from the first and second oil diffusers. In some embodiments, the housing comprises a total of three or more oil diffusers.

Another aspect of the present disclosure relates to an essential oil atomizer, comprising a housing connectable to a mixing shell, the mixing shell defining a mixing chamber and a shell outlet, at least two oil diffusers connected to the housing. Each of the at least two oil diffusers can comprise an oil receptacle, an atomizer nozzle assembly configured to atomize oil from the oil receptacle in a gas, and a spray outlet through which the atomized oil and gas can be configured to be expelled into the mixing chamber. The atomized oil and gas from each of the at least two oil diffusers can be configured to be combined in the mixing chamber and to be expelled through the shell outlet.

In some embodiments, the essential oil atomizer can comprise a heating assembly configured to raise a temperature of the oil. The heating assembly can comprise a first heater configured to raise the temperature of a first oil diffuser of the at least two oil diffusers, and a second heater configured to raise the temperature of a second oil diffuser of the at least two oil diffusers. The heating assembly can be configured to heat gas expelled through each of the atomizer nozzle assemblies. The heating assembly can be configured to raise the temperature of the oil by heating the oil before or while the oil flows to the nozzle assembly. The heating assembly can comprise a first heating element configured to at least partially surround one of the oil receptacles, and a second heating element configured to at least partially surround another of the oil receptacles.

Another aspect of the present disclosure relates to an essential oil atomizer, comprising a housing having a first mounting location and a second mounting location, first and second oil diffusers located within the housing, the first oil diffuser being positioned in the first mounting location, the second oil diffuser being positioned in the second mounting location, wherein the first and second oil diffusers are removable from the first and second mounting locations. Each of the first and second oil diffusers can comprise an oil receptacle and an atomizer nozzle assembly in fluid communication with the oil receptacle, the atomizer nozzle assembly configured to atomize oil.

In some embodiments, the essential oil atomizer can further comprise a third oil diffuser, wherein the third oil diffuser can be connectable to the housing in the first mounting location upon removal of the first oil diffuser from the first mounting location. The third oil diffuser can have different properties relative to the first oil diffuser. The atomizer nozzle assembly can comprise an oil nozzle and a gas nozzle, wherein the oil nozzle can be configured to be in fluid communication with the oil receptacle, and the gas nozzle can be configured to expel the gas across the oil nozzle. The housing can comprise a total of three or more mounting locations for a total of three or more oil diffusers.

The above summary of the present invention is not intended to describe each embodiment or every implementation of the present invention. The Figures and the detailed description that follow more particularly exemplify one or more preferred embodiments.

BRIEF DESCRIPTION OF THE DRAWINGS

The accompanying drawings and figures illustrate a number of exemplary embodiments and are part of the specification. Together with the present description, these drawings demonstrate and explain various principles of this disclosure. A further understanding of the nature and advantages of the present invention may be realized by reference to the following drawings. In the appended figures, similar components or features may have the same reference label.

Figure 1:
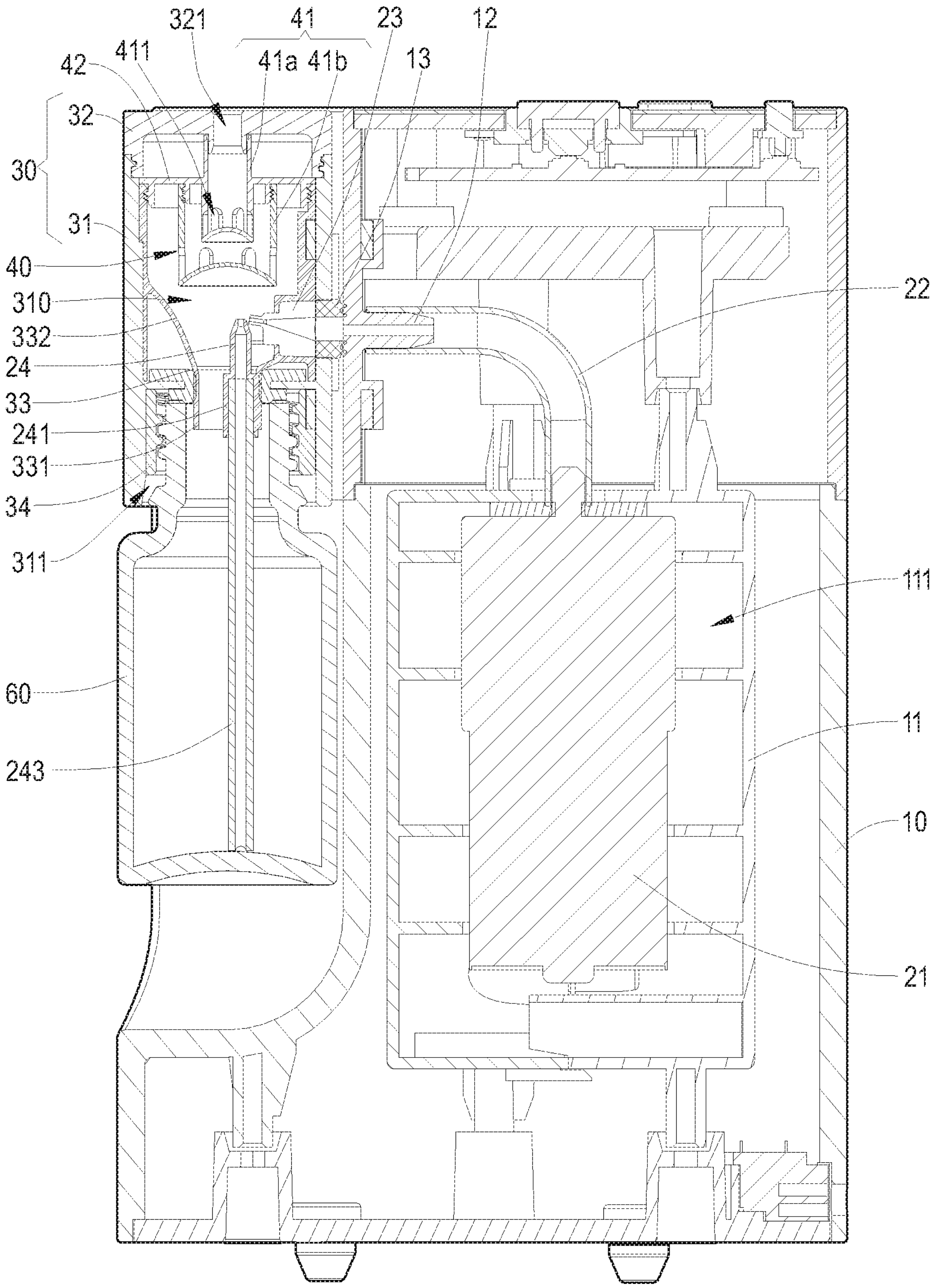
FIG. 1 is a sectional structure view of the essential oil atomizer provided by a first embodiment of the present invention.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

A conventional essential oil atomizer/nebulizer typically ejects a high-speed airflow to extract an essential oil from an essential oil bottle and to transfer the essential oil out of the atomizer into the surrounding atmosphere. However, this atomization method can result in larger droplets of essential oil in the atomized gas, so the atomization performance is poor and oil is inefficiently distributed. The large essential oil droplets can be wasted if they are dispensed. To reduce the waste of essential oils, a filter is often used for filtering the atomized airflow mixed with the essential oil droplets so as to recycle the essential oil droplets. However, since the space of the essential oil atomization chamber is generally small, the mixed airflow may directly hit and accumulate in an area of the sidewall of the atomization chamber facing the gas nozzle. With subsequent airflow hitting the same area, the essential oil droplets in the area can be blown and splashed to the filter, thereby blocking the filter, reducing the efficiency of filtration, and causing waste.

These issues are amplified and aggravated when the essential oils have high viscosity or high molecular stability. These thicker oils are much more difficult to draw through a tube or channel from an oil reservoir to the air flow. They are also less effectively atomized and diffused by the airflow, so the atomizer less effectively distributes the oil using the airflow.

Compared to conventional essential oil atomizers, airflow-guided essential oil reflux-type atomizers of the present invention can provide many beneficial effects. First, by providing the filter atomization mechanism in the atomization chamber, when an airflow is pumped out of the gas pump through the gas nozzle, the airflow extracts the essential oil from the essential oil bottle through the oil nozzle, and atomizes the essential oil to form a mixed airflow. When the mixed airflow passes through each of the filter housings of the filter atomization mechanism, successively larger essential oil droplets in the airflow are filtered by each of the filter housings to be recycled, thereby reducing waste of the essential oil, while smaller atomized essential oil droplets will pass through the through hole of each of the filter housings to be dispensed out the atomizer into the environment. When the essential oil droplets in the airflow are located in each of the through holes, the pressure difference between two sides of the filter housing can create an airflow in each of the through holes to re-atomize these essential oil droplets to improve the atomization performance.

Second, in embodiments having a guide board and filter in the atomization chamber, the mixed airflow (which includes a mixture of the airflow from a gas pump and essential oil from the oil bottle) can hit the guide board and be guided to flow upward to the filter atomization mechanism, where the larger essential oil droplets are filtered and recycled to reduce waste. At the same time, the guide board can also collect some of the essential oil droplets from the mixed airflow, reducing oil splashing which may block the filter to ensure filtration efficiency.

It is noted that when a component is referred to as being "fixed to," "installed on," "arranged on" or "disposed on" another component, it can be directly or indirectly fixed on another component. When a component is referred to as being "connected to" another component, it can be directly or indirectly connected to the other component.

In addition, the terms "first" and "second" are for illustrative purposes only and should not be construed as indicating or implying a relative importance or indicating the quantity of technical features. Therefore, a feature that is qualified as "first" and "second" may expressly or implicitly include one or more of such a feature. In the description of the present invention, "multiple" means two or more, unless otherwise specifically defined.

Unless specified otherwise, it should be understood that, "length", "width", "upper", "lower", "front", "back", "left" and "right", "vertical", "horizontal", "top", "bottom", "inside", "outside" and other terms indicating the orientation or positional relationship are used to refer to orientation or positional relationship shown in the drawings, only for the purpose of facilitating and simplifying the description of the invention, instead of indicating or implying that the indicated device or component must have a specific orientation and constructed and operated in a particular orientation, and therefore cannot be construed as limiting.

In the description of the present invention, it should be noted that the terms "install," "connected," and "connect" should be interpreted broadly unless specifically defined or limited otherwise. For example, the components may be fixedly connected or they may be detachable connected, or integral connected. The connection can be mechanical or electrical. The connection can be direct or indirect (connected through an intermediary). It can also be the internal communication of two components or the interaction between two components. Those of ordinary skill in the art can understand the specific meanings of the above terms in the present disclosure according to specific circumstances.

Embodiment One

Figure 2:
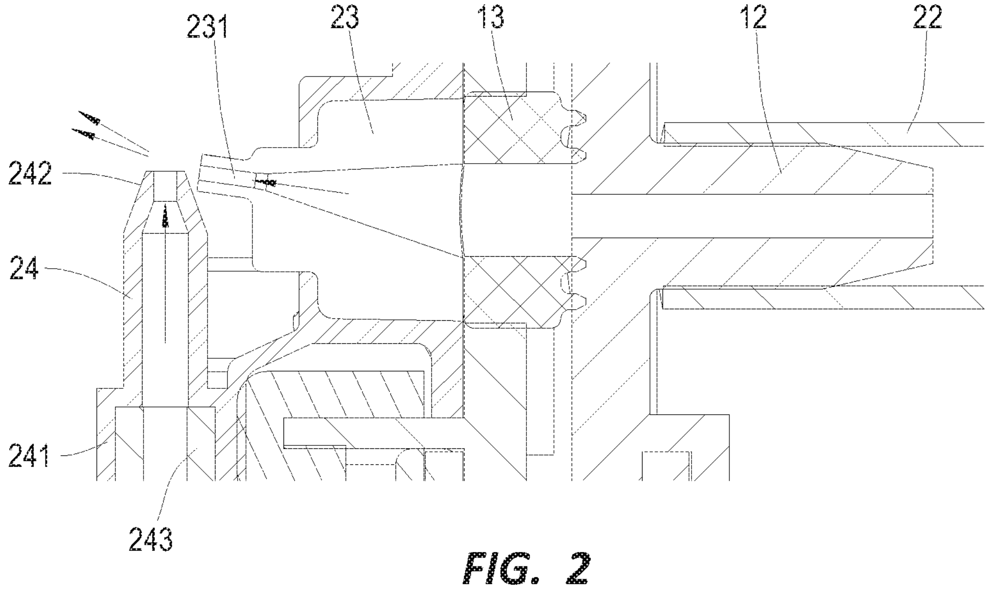
FIG. 2 is an enlarged view of the gas nozzle and the oil nozzle of the essential oil atomizer shown in FIG. 1.
Figure 3:
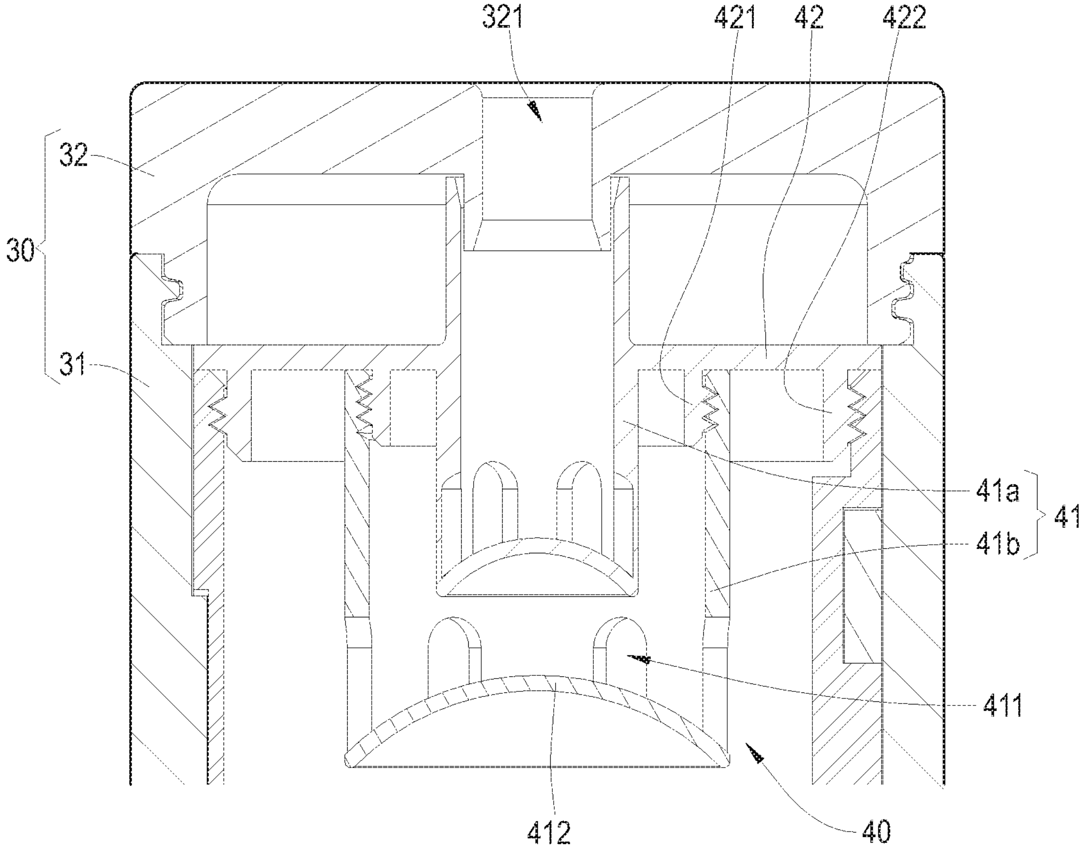
FIG. 3 is an enlarged view of the filter atomization mechanism of the essential oil atomizer shown in FIG. 1.
Figure 4:
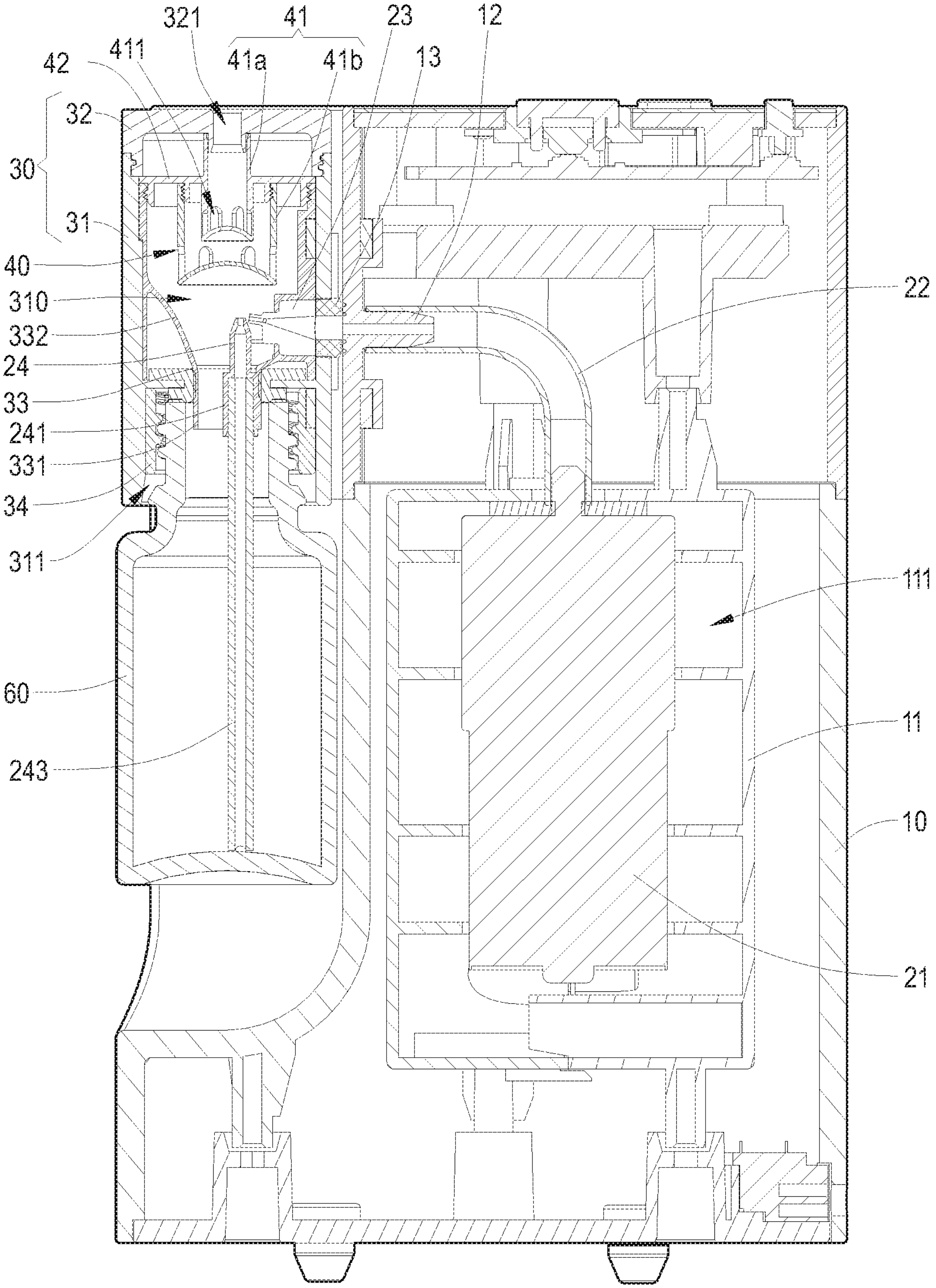
FIG. 4 is a sectional view of the essential oil atomizer provided by a second embodiment of the present invention.

FIGS. 1 through 3 represent an embodiment of an essential oil reflux-type atomizer of the present invention. The essential oil reflux-type atomizer includes a chassis 10, a housing 30, a gas pump 21, a gas tube 22, a gas nozzle 23, an oil nozzle 24, and a filter atomization mechanism 40. The housing 30 includes an atomization chamber 310 and a dispensing opening 321 connected to the atomization chamber 310. A lower end of the housing 30 includes a connection opening 311 for cooperatively connecting the essential oil bottle 60. The housing 30 is installed on the chassis 10. The gas pump 21 is also installed in the chassis 10, which supports and protects the gas pump 21. One end of the gas tube 22 is connected to the gas pump 21, and the other end of the gas tube 22 is connected to the gas nozzle 23. The oil nozzle 24 is located at a position corresponding to the connection opening 311 so that when the connection opening 311 is connected to the essential oil bottle 60, the essential oil can be extracted from the essential oil bottle 60 through the oil nozzle. The upper end of the oil nozzle 24 is protruded into the atomization chamber 310. An outlet 231 of the gas nozzle 23 is located adjacent to the upper end of the oil nozzle 24 and is configured to direct an airflow exiting the gas pump to the upper end of the oil nozzle. Without wishing to be bound by theory, it is believed that, when the gas pump 21 provides high pressure airflow and ejects the airflow from the gas nozzle 23, a negative pressure is formed at the upper end of the oil nozzle 24 to extract essential oil from the essential oil bottle 60 via the oil nozzle 24. The extracted essential oil droplets can then be atomized by the high-speed airflow from the gas nozzle 23 to form a mixed airflow containing essential oil droplets, which increases the pressure in the atomization chamber 310. Because the connection opening 311 and the essential oil bottle 60 are connected, the high-pressure mixed airflow in the atomization chamber 310 will be forced through the dispensing opening 321 to be dispensed into the environment.

The filter atomization mechanism 40 is arranged in the atomization chamber 310 in the housing 30 and is supported by the housing 30. The filter atomization mechanism 40 is used to filter the essential oil droplets in the airflow flowing from the atomization chamber 310 to the dispensing opening 321. When the mixed airflow in the atomization chamber 310 flows toward the dispensing opening 321, it needs to pass through the filter atomization mechanism 40, where the mixed airflow may be filtered by the filter atomization mechanism 40 to recycle larger essential oil droplets and reduce the waste of essential oils while the smaller essential oil droplets will pass through the filter atomization mechanism 40 to be dispensed through the dispensing opening 321.

In general, the filter atomization mechanism 40 includes a plurality of (e.g., two, three, or four) filter housings 41. In some embodiments, when the airflow in the atomization chamber 310 flows toward the dispensing opening 321, it passes through the filter housings 41 successively. The lower ends (e.g., at the bottom of the cylinders) of the filter housings 41 include one or more (e.g., two, three, or four) through holes 411 for filtering the essential oil droplets in the airflow. When the airflow containing essential oil droplets passes through each of the filter housings 41 successively, the larger essential oil droplets in the mixed airflow are filtered by each of the filter housings 41 and can flow back to the oil bottle through the return funnel due to gravity. The smaller essential oil droplets can pass through the through hole 411 of each of the filter housings 41 to be dispensed through the dispensing opening 321. As discussed above, the airflow from the gas nozzle 23 increases the pressure in the atomization chamber outside the filter housings 41. Without wishing to be bound by theory, it is believed that the pressure difference at two sides of the filter housing 41 creates an airflow in each of the through holes 411, such that the essential oil droplets in the through holes 411 are re-atomized by the airflow to improve the atomization efficiency. As a result, using the plurality of filter housings 41 can better filter larger essential oil droplets, further reduce waste, and improve the efficiency of filtration. In addition, it is believed that, compared to a conventional system without a filter housing, using the filter housing 41 can better return the essential oil liquid accumulated therein, and avoid oil attachment to the filter atomization mechanism 40, and thus better recycle the filtered essential oil droplets and further reduce the waste of essential oils.

Compared to a conventional atomizer, the essential oil reflux-type atomizer of the present invention has one or more of the following beneficial effects: when the gas nozzle 23 blows out the airflow, essential oil is extracted from essential oil bottle through the oil nozzle 24, and mixed and atomized by the airflow to form a mixed airflow. When the mixed airflow passes through each of the filter housings 41 of the filter atomization mechanism 40 successively, the larger essential oil droplets in the airflow can be filtered by each of the filter housings 41 and recycled, thereby reducing waste of the essential oil. The smaller essential oil droplets can pass through each of the filter housings 41 and dispensed into the environment. The pressure difference between the two sides of the filter housing 41 creates an airflow in each of the through holes 411, therefore the essential oil droplets in the through hole 411 are re-atomized by the airflow to improve the atomization efficiency.

Further, FIGS. 1 and 3 show embodiments in which each of the filter housings 41 is cylindrical, the diameters of a plurality of the filter housings 41 are reduced successively, a plurality of the filter housings 41 are concentrically arranged, and the two adjacent filter housings 41 include an inner layer filter housing 41*a* is inserted into an outer layer filter housing 41*b*. The inner layer filter housing 41*a* is connected with the dispensing opening 321. The filter housings 41 are generally simple to manufacture, and easy to install. The filter housings 41 are located in the atomization chamber 310, facilitating the mixed airflow in the atomization chamber 310 to enter the filter housings 41 to be filtered and atomized. In addition, the filter housings 41 are arranged in a cylindrical shape, and one or more through holes 411 are arranged at the lower end of the filter housings 41. The inner layer filter housing 41*a* is inserted into the outer layer filter housing 41*b*. Without wishing to be bound by theory, it is believed that, when the mixed airflow enters the outer layer filter housing 41*b* from the through holes 411, it rotates and/or turbulently flows along the outer wall of the inner layer filter housing 41*a*. Thus, the atomized essential oil can rapidly diffuse, and the larger essential oil droplets will hit the outer surface of the inner layer filter housing 41*a* due to inertia to be blocked and filtered to improve the filtering effect. In addition, when the gas pump is not in use, the essential oil collected in the filter housings 41 forms larger droplets and returns to essential oil bottle 60 through the through holes of the filter housings 41 due to gravity and can be re-used. In some embodiments, a plurality of boards with holes (e.g., in addition to or in lieu of filter housings 41) may be used to filter the essential oil droplets in the atomization chamber. In other embodiments, the filter housings 41 may also be cup-shaped with the central part of the bottom arched downward.

In this embodiment, the number of the filter housings 41 is two, and the inner layer filter housing 41*a* is inserted into the outer layer filter housing 41*b*. In other embodiments, the number of the filter housings 41 can be three, four, or more.

Further, as shown in FIG. 3, the filter atomization mechanism 40 further includes a fixing board 42, which includes a plurality of connection rings 421 for connecting the upper ends of the filter housings 41 to the housing 30. With the connection rings 421, each of the filter housings 41 can be conveniently connected to the fixing board 42, either integrally or through threaded engagement. The fixing board 42 can be installed in the atomization chamber 310 so that the filter housings 41 can be installed in the atomization chamber 310. In some embodiments, the fixing board 42 includes a passing hole. The passing hole can be located in the innermost connection ring 421 so that when the innermost layer filter housing 41 is installed on the fixing board 42, the passing hole can receive the innermost layer filter housing 41, and thus the innermost layer filter housing 41 is connected with the dispensing opening 321.

Further, as shown in FIG. 3, the fixing board 42 can further include a fixing ring 422 around the connection rings 421. The fixing ring 422 can be connected with an inner wall of the atomization chamber 310. It is convenient to install and secure the fixing board 42 in the atomization chamber 310 through the fixing ring 422.

Furthermore, the fixing ring 422 may have installation threads. The inner wall of the atomization chamber 310 can have corresponding threads for threaded connection with the fixing ring 422.

Further, in some embodiments, one or more of the connection rings 421 may include a first thread, and the upper ends of the corresponding filter housings 41 may include a second thread corresponding to the first thread. The structure can be conveniently manufactured by methods known in the art. One or more of the filter housings 41 can be conveniently connected with the corresponding connection rings 421 through threaded engagement.

Further, as shown in FIGS. 1 and 2, the innermost layer filter housing 41 and the fixing board 42 are integrally formed. Forming the fixing board 42 integrally with the innermost layer filter housing 41 can ensure the connection strength between the innermost layer filter housing 41 and the fixing board 42. In this structure, the innermost connection ring 421 can be used as a sidewall of the inner layer filter housing 41 to reduce the space occupied. In other embodiments, the fixing board 42 and the innermost layer filter housing 41 can be two separate parts and can be connected through threaded engagement described above.

Further, as shown in FIGS. 1 and 2, a bottom board 412 of each of the filter housings 41 is curved, with the central part of the bottom board 412 arched upward. The through holes 411 are located at the lower end (e.g., defined by the sidewall and the bottom board) of the sidewall of the filter housings 41. The bottom board 412 of each of filter housings 41 is arched to allow the essential oil liquid collected in the filter housing 41 to flow toward the through holes 411 and be discharged back into the essential oil bottle 60.

Further, the through holes 411 of each of the filter housings 41 are located at the lower end of the sidewall (e.g., at the lower one-third of the sidewall) of each filter housing 41, making it convenient for manufacturing and also convenient for filtration and recycling of the essential oil droplets. Furthermore, when the bottom board 412 of a filter housing 41 has an upwardly arched arc surface, the arc surface can also guide the airflow flowing from each of the through holes 411 into the filter housing 41.

Further, the through holes 411 of two adjacent filter housings 41 can be mutually staggered. In such embodiments, when the airflow passes through the through hole 411 of the outer layer filter housing **41*b*, the larger essential oil droplets are blown onto the outer sidewall of the inner layer filter housing 41*a* to be blocked and collected to achieve better filtration. Smaller droplets have less mass and thus less inertia so that they can change directions more easily and stay with the airflow. In some embodiments, the through holes 411 in two adjacent filter housings 41 can have successively reduced diameters to filter larger essential oil droplets. For example, the diameters of the through holes 411 in the inner layer filter housing 41*a* can be smaller than those of the through holes 411 in the outer layer filter housing 41*b*. In some embodiments, the diameter of the though holes 411 of the innermost filter housing 41 ranges can be 1.6 mm-2.0 mm (e.g., 1.8 mm) while the diameter of the though holes 411 of the immediate outer filter housing 41 is can be 2.0 mm-2.4 mm (e.g., 2.2 mm). In such embodiments, the through holes 411 in the inner layer filter housing 41*a* and outer layer filter housing 41*b*** can be either centrally aligned or staggered (i.e., not centrally aligned).

Further, in two adjacent filter housings 41, the bottom board of the inner layer filter housing **41*a* can be spaced from the bottom board 412 of the outer layer filter housing 41*b* so that the airflow in the gap between the inner layer filter housing 41*a* and the outer layer filter housing 41*b*** can be increased, enhancing the filtration and recycling of the essential oil droplets.

Further, in two adjacent filter housings 41, the closest distance between the sidewall of the inner layer filter housing **41*a* and the sidewall of the outer layer filter housing 41*b* can range from at least 1.5 mm (e.g., at least 2 mm or at least 3 mm) to at most 10 mm (e.g., at most 9 mm or at most 8 mm). Without wishing to be bound by theory, it is believed that controlling the above distance to 1.5-10 mm can be important to minimize excessive noise when the essential oil atomizer is being used. In a preferred embodiment, the closest distance between the sidewalls of two adjacent filter housings 41** is 2.2 mm.

Further, as shown in FIGS. 1 and 2, the axial direction of the outlet 231 of the gas nozzle 23 is directed toward the top of the upper end of the sidewall 242 of the oil nozzle 24. The outlet axis of the gas nozzle and the outlet axis of the oil nozzle form an angle that is less than 90 degrees. When the airflow is ejected from the outlet 231 of the gas nozzle 23, the airflow can cover the upper end of the oil nozzle 24 to better form a negative pressure (e.g., due to Bernoulli effect) at the upper end of the oil nozzle 24, which can extract essential oil from the essential oil bottle 60. At the same time, the top of the sidewall 242 of the oil nozzle 24 can change the direction of the airflow ejected from the gas nozzle 23 (e.g., by blocking at least some of the airflow), thereby improving the atomization of the essential oil droplets drawn from the oil nozzle 24.

Further, the airflow ejected from the outlet 231 of the gas nozzle 23 is directed toward the top of the upper end of the sidewall 242 of the oil nozzle 24 from a lower position (e.g., the outlet 231 can be at a lower position than the oil nozzle 24). This arrangement can prevent the airflow ejected by the gas nozzle 23 from being blown into the oil nozzle 24, thereby facilitating extraction of the essential oil from the essential oil bottle and blowing the essential oil upward for better atomization. Further, in this embodiment, the sidewall 242 of the upper end of the oil nozzle 24 is conically shaped, guiding upward the airflow from the gas nozzle 23 so that the airflow can better atomize the essential oil drawn from the oil nozzle 24. In other embodiments, the sidewall 242 of the upper end of the oil nozzle 24 may also be a dome in shape.

Further, as shown FIG. 1, a lower end of the atomization chamber 310 includes a return funnel 33 with an outlet tube 331 at the bottom. The outlet tube 331 protrudes into the connection opening 311. The oil nozzle 24 is integrally connected to the outlet tube 331. When the connection opening 311 is connected with the essential oil bottle 60, the outlet tube 331 of the return funnel 33 is protruded into the essential oil bottle 60, so that the recycled essential oil droplets in the atomization chamber 310 can better return to the essential oil bottle 60.

Further, in this embodiment, the lower end of the return funnel 33 is connected with the inner wall of the atomization chamber 310, such that the essential oil liquid accumulated on the inner wall of the atomization chamber 310 can be easily returned to the essential oil bottle 60.

Further, as shown in FIG. 1, a lower end of the oil nozzle 24 is connected with a connection sleeve 241. An oil tube 243 can be detachably inserted in the connection sleeve 241 and can be in fluid communication with oil nozzle 24 such that essential oil can be extracted from essential oil bottle 60 to the atomization chamber 310 through the oil tube 243 and oil nozzle 24. In some embodiments, oil tubes 243 of different lengths can be used to fit different essential oil bottles 60, enhancing the adaptability of the design.

Further, as shown in FIG. 1 represent a connection tube 12 is arranged at the corresponding position of the chassis 10 to allow the gas tube 22 to be connected with the gas nozzle 23, thereby allowing airflow to travel from the gas pump 21 through the gas tube 22 and connection tube 12, and to be ejected from gas nozzle 23. The connection tube 12 is arranged in the chassis 10 such that the gas tube 22 can be securely attached to it to deliver airflow from the gas pump 21 into the atomization chamber 310.

Furthermore, in this embodiment, a sealing ring 13 is arranged between the gas nozzle 23 and the connection tube 12 to improve the sealing and minimize leaks of the connection so that substantially all the airflow in the gas tube 22 can flow through the gas nozzle 23. It is believed that this structure simplifies the manufacture and connection of the housing 30 and the chassis 10. In other embodiments, the gas nozzle 23 can also be directly connected to the gas tube 22 without using a connection tube 12. In some other embodiments, the gas nozzle 23 and the connection tube 12 can be integrally formed as a part of the chassis 10 (e.g., without using a sealing ring 13).

Further, as shown in FIGS. 1 and 3, the housing 30 includes a main housing 31 installed on the chassis 10 and an outer cover 32 installed on the main housing 31. The atomization chamber 310 is formed in the main housing 31, the outer cover 32 covers the atomization chamber 310. The outer cover 32 includes the dispensing opening 321 at the top of the housing 30. The connection opening 311 is arranged at a bottom of the main housing 31. This structure simplifies the manufacture of the housing 30 and the assembly of the parts. For example, it simplifies the installation of the oil nozzle 24, gas nozzle 23 and the filter atomization mechanism 40 onto the housing 30.

Further, as shown in FIGS. 1 and 3, the connection opening 311 is provided with a thread sleeve 34 for connecting the essential oil bottle 60. The thread sleeve 34 is arranged in the connection opening 311 to ensure easy installation and replacement of the essential oil bottle 60.

Further, as shown in FIG. 1, the chassis 10 includes a supporting frame 11. The gas pump 21 is installed on the supporting frame 11 for better fixation. The supporting frame 11 includes a plurality of heat dissipation channels 111 to improve the heat dissipation efficiency.

In some embodiments, the gas pump 21 can be a diaphragm pump. Of course, in other embodiments, the gas pump 21 can be other types of pumps, such as centrifugal pump, piston pump, and the like.

Embodiment Two

Referring to FIGS. 1 and 3, the essential oil reflux-type atomizer provided by embodiment two can have one or more of the following differences from embodiment one:

In some embodiments, a side of the atomization chamber 310 facing the gas nozzle 23 is provided with an optional guide board 332. The guide board 332 forms an inclined plane relative to the axial direction of an outlet 231 of the gas nozzle 23 and integrally connected with or formed on a sidewall of the atomization chamber 310. The guide board 332 is configured to guide the airflow jetted by the gas nozzle 23 upward. When the gas nozzle 23 ejects the air flow and extracts the essential oil to form the mixed airflow, the mixed airflow can flow towards the guide board 332 which can better guide the mixed airflow to the filter atomization mechanism 40, thereby facilitating filtration in filter atomization mechanism 40. In addition, the guide board 332 can also collect part of the essential oil droplets from the mixed airflow, reducing oil splashing (which may block the filter atomization mechanism 40) and ensuring filtration efficiency.

Further, the guide board 332 can be connected to an upper end of the return funnel 33. This structure can make it easier for the oil droplets accumulated on the guide board 332 to return to the essential oil bottle 60 through the return funnel 33, thereby improving the efficiency of the recycling process. Further, the guide board 332 may be integrally formed with the return funnel 33 to simplify manufacture, installation and fixation.

Further, in some embodiments, the guide board 332 is flat. In some embodiments, the guide board 332 is curved.

Further, the angle between an extension line of an outlet 231 axis of the gas nozzle 23 and the tangent line at the intersection of this extension line and the guide board 332 can range from at least 15 degrees (e.g., at least 20 degrees or at least 25 degrees) to at most 35 degrees (e.g., at most 30 degrees or at most 25 degrees). For example, the angle can be about 32 degrees. In this arrangement, the guide board 332 can better guide the airflow to the guide board 332, and reduce the impact of the airflow to the guide board 332.

Further, in one specific embodiment, the closest distance between the outermost filter housing 41 and the oil nozzle 24 is at least 2 mm (e.g., at least 3 mm or at least 4 mm). This distance can reduce the oil splashing on the filter housings 41 and avoid congestion at the filter atomization mechanism 40.

The other structures of the essential oil reflux-type atomizer in the present embodiment can be the same as the corresponding structures of the essential oil reflux-type atomizer in embodiment one, and the details will not be repeated here.

The aforementioned embodiments are only preferred embodiments of the present invention, and are not intended to limit the present invention. Any modification, equivalent replacement, improvement, and so on, which are made within the spirit and the principle of the present invention, should be included in the scope of the present invention.

Essential oil atomizers, including reflux-type atomizers, can have difficulty atomizing and diffusing essential oils that have high viscosity for high molecular weight. For example, in such cases, the essential oil can have difficulty traveling up an oil tube 243 or through an oil nozzle 24. Additionally, the oil can be less likely to atomize into droplets as result of airflow passing through the gas nozzle 23. Oil droplets that are atomized from the oil nozzle 24 can also be larger than desired and can therefore accumulate more easily within the atomization chamber 310 or on the filter housings 41.

FIGS. 6-13 show embodiments of essential oil atomizers configured to help reduce the viscosity of denser and stickier essential oils and to thereby improve flow from an oil bottle 60 (i.e., an oil receptacle or oil container) through the oil tube 243 and oil nozzle 24, improve droplet formation (i.e., increasing the volume of oil diffused from the nozzle (or the rate of oil diffused over time) and/or decreasing the size of the oil droplets formed by the gas flow), and reduce oil accumulation in the atomization chamber 310 and filter housings 41. These additional embodiments can include heaters having heating elements configured to (a) heat the oil (or its container) directly, thereby reducing the oil's internal viscosity, (b) heat a chamber in which the oil or its container is positioned in a housing or chassis of the atomizer, thereby indirectly reducing the oil's internal viscosity, (c) heat a nozzle, tube, or other passage through which the oil is drawn after it leaves its container, thereby reducing viscosity locally within that nozzle, tube, or passage, (d) heat the gas or passages through which the gas passes before it comes into contact with oil so that the heated gas can reduce the viscosity of the oil when it comes into contact with the oil (i.e., when the oil is being atomized at the oil nozzle), (e) heat up multiple portions or passageways within the atomizer, or (f) implement combinations or subcombinations of (a) through (e) to improve atomization efficiency for otherwise potentially stubborn or problematic essential oils. Heaters disclosed herein can be electronically controlled to manage the temperature to which the oil is heated, to improve energy efficiency, and to limit or prevent overheating.

Various types of heaters can be used in atomizers. In some embodiments, including the embodiments of FIGS. 6-13, a heater can comprise resistive metal or metallic wires (e.g., wires formed into resistive heating coils), ceramic compound blocks or units (e.g., comprising Positive Temperature Coefficient (PTC) ceramic), thick film heaters, resistive polymer heating elements (e.g., conducting PTC rubber), composite heating elements, incandescent or other radiative heating elements, liquid-based heating elements, heat pumps, similar types of heating elements, and combinations thereof. Heaters can be configured to raise the temperature of the essential oil in its container (or where it is being atomized) to a temperature within a range extending from about 30 degrees Celsius to about 40 degrees Celsius. In some embodiments, the temperature of the oil in the container or reservoir is raised by the heater to be within a range of about 35 degrees Celsius to about 40 degrees Celsius. Therefore, depending on the configuration of the heater, the temperature of the heater can be configured to reach a temperature within a range of about 55 degrees Celsius to about 85 degrees Celsius, and heat from the heater can then be transferred to the oil to cause the oil temperature to increase as indicated above. Then the heated, atomized oil droplets can have an elevated temperature that remains elevated (e.g., remains above ambient room temperature) as they pass through the atomization chamber, as they pass through the filter housings (if any), as they exit the atomizer, or as they cycle through multiple stages of this atomization and diffusion process.

Figure 6:
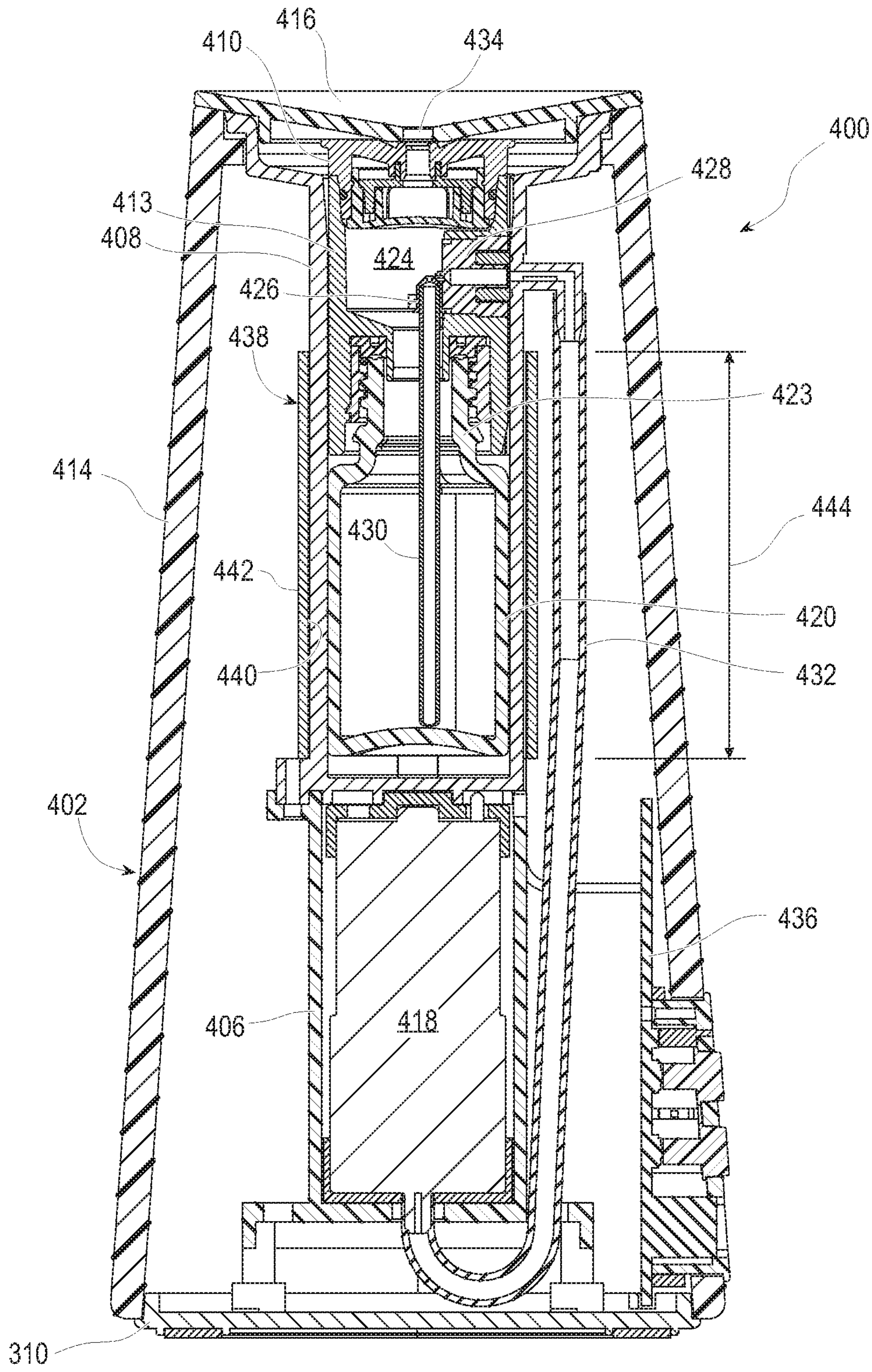
FIG. 6 is a side section view of an upper end of an essential oil atomizer of the present disclosure.

FIG. 6 shows an example embodiment of an essential oil atomizer 400 having a heater according to the present disclosure. The atomizer can comprise a chassis 402 including a base 404, a lower housing 406, an upper housing 408, a filter housing 410, an atomization housing 413, an outer shell 414, and a top cap 416. A pump 418 (i.e., a gas or air pump, an air or gas compressor, or similar air flow provider) can be located within the lower housing 406, and oil receptacle 420 can be located in the upper housing 408. A top end 423 of the oil receptacle 420 can mate with and connect to a lower end of the atomization housing 413.

Figure 5:
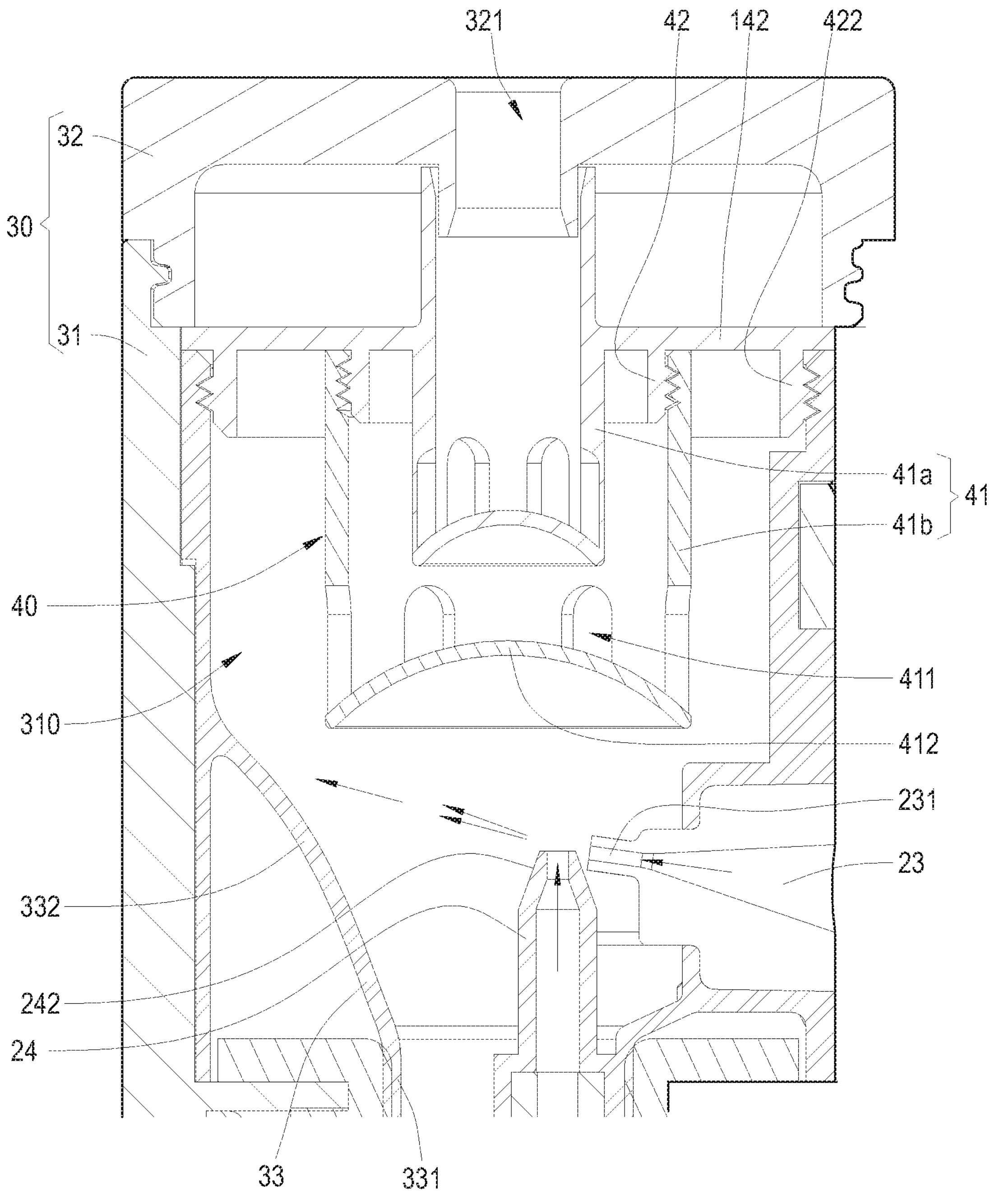
FIG. 5 is an enlarged view of the gas nozzle and the oil nozzle of the essential oil atomizer shown in FIG. 4.

The atomization housing 413 can have an atomization chamber 424. The oil nozzle 426 and gas nozzle 428 can have outlets within the atomization chamber 424, similar to the outlets (e.g., 231 and end of 24) shown in FIG. 5. The oil nozzle 426 and gas nozzle 428 can collectively be referred to as an atomizer nozzle assembly that is configured to atomize oil at the oil nozzle 426 by expelling a gas (e.g., compressed air) from the gas nozzle 428 into contact with or over the surface of the oil in the oil nozzle 426. The oil nozzle 426 can be in fluid communication with an oil tube 430 configured to extend into the oil receptacle 420. The gas nozzle 428 can be connected to a gas tube 432 (i.e., a gas or air line, gas or air supply line, or gas or air passage) that receives output (i.e., gas flow) from the pump 418. The parts and features of this essential oil atomizer 400 can have similar functions and can perform similar effects as their corresponding parts described in previous embodiments shown above.

Additionally, the base 404, the lower housing 406, the upper housing 408, the top 416, the atomization housing 413, and the outer shell 414 can all be concentrically aligned along a central vertical axis extending through the atomizer 400. The positioning of these parts can reduce the overall width footprint of the atomizer 400, thereby making it more compact and giving it aesthetic appeal. In an example embodiment, the outer shell 414 can be removed from the base 404 and other parts such as the upper and lower housings 406, 408 can be separated to provide access for a user to insert and remove the oil receptacle 420, e.g., to change the receptacle 420 or to refill oils in the receptacle 420. In some embodiments, a user can refill the oil receptacle 420 by pouring oil through the central vent opening 434 in the top cap 416, which allows the oil to pass through the atomization chamber 424 into the oil receptacle 420. In some cases, the oil receptacle 420 can be removed, and a non-removable and integrated chamber can be used within the upper housing 408 or atomization housing 413 that is configured to hold and retain oil until it is atomized and diffused from the atomizer 400 or until the oil is poured out. Thus, a bottle-shaped oil receptacle 420 can be used for convenience but is optional.

The atomizer 400 can also include an electronics unit 436 (e.g., a printed circuit board (PCB), power electronics, buttons, connectors, etc.) in electrical communication with the pump 418 and configured to control the operation of the pump 418, the amount of gas flow produced by the pump 418, and similar functions. The electronics unit 436 can also be electrically connected to a heater 438 that is horizontally aligned with (i.e., is centered at roughly the same height in the atomizer 400 as the electronics unit 436) and substantially surrounds the oil receptacle 420. A set of electrical controls or switches (e.g., 450 in FIG. 7) can be used to provide user input to the electronics unit 436.

The heater 438 can include a heating element 440 positioned on a radially internal side of the heater 438 relative to a central axis of the atomizer 400 and relative to the central axis of the upper housing 408 (i.e., a central axis extending vertically through the central vent opening 434). The heater 438 can also include an insulator 442 externally radially surrounding the heating element 440. As explained above, the heating element 440 can be a resistive heating element or other type of electronic heater configured to receive power from the electronics unit 436 to generate heat. The heat generated by the heating element 440 can be transferred (e.g., via conduction, radiation, and convection) through the upper housing 408, the walls of the oil receptacle 420, and into oil within the oil receptacle 420, thereby heating and raising the internal temperature of oil in the oil receptacle 420. The insulator 442 can help improve efficiency of the heating element 440 by limiting heat transfer in a radially outward direction from the oil receptacle 420. The insulator 442 can comprise a thermally insulating material such as fiberglass, foam rubber, ethylene vinyl acetate (EVA) foam, urethane foam, cork, polystyrene foam, cellulose, similar materials, and combinations thereof.

The heater 438 can have a heater length dimension 444 measured extending parallel to the vertical longitudinal axis of the oil receptacle 420 or parallel to a central longitudinal axis of the oil tube 430. The length dimension 444 can be substantially equal to an overall length/height dimension of the oil receptacle 420, as shown in FIG. 6. In this manner, the heater 438 can apply heat along the overall length of the oil receptacle 420 and thereby ensure that all of the oil in the receptacle 420 is heated by the heater 438.

In some embodiments, the length dimension 444 can extend along less than the entire length of the oil receptacle 420, such as, for example, along half of the length of the receptacle 420 or less. In some embodiments, the heater 438 can extend along only an upper end of the receptacle 420 to heat the oil just before it enters the oil nozzle 426. In some embodiments, the heater 438 can extend along only the lower end of the receptacle 420. This can be beneficial to apply heat to oil that accumulates at the bottom of the receptacle 420 and to allow the oil to start to cool as it moves up the oil tube 430 before being atomized at the oil nozzle 426.

In some embodiments, the heater 438 can be positioned radially between the upper housing 408 and the oil receptacle 420. This can help improve the efficiency of heat transfer into the oil receptacle 420. In embodiments where the heater 438 is positioned external to the upper housing 408, as shown in FIG. 6, the heater 438 can be protected by the upper housing 408 from potential damage and wear that can occur when a user removes and inserts an oil receptacle 420 while operating the atomizer 400 (e.g., when refilling or changing the oil receptacle). In some embodiments, the heater 438 can be positioned beneath the oil receptacle 420 and can therefore apply heat to the bottom of the oil receptacle 420. In this case, the heater 438 can be smaller and the external width of the upper housing 408 can be reduced. The size of the heater 438 can be configured to apply sufficient heat to the oil to raise its temperature to a range such as about 30 degrees Celsius to about 40 degrees Celsius at the oil nozzle 426.

Figure 7:
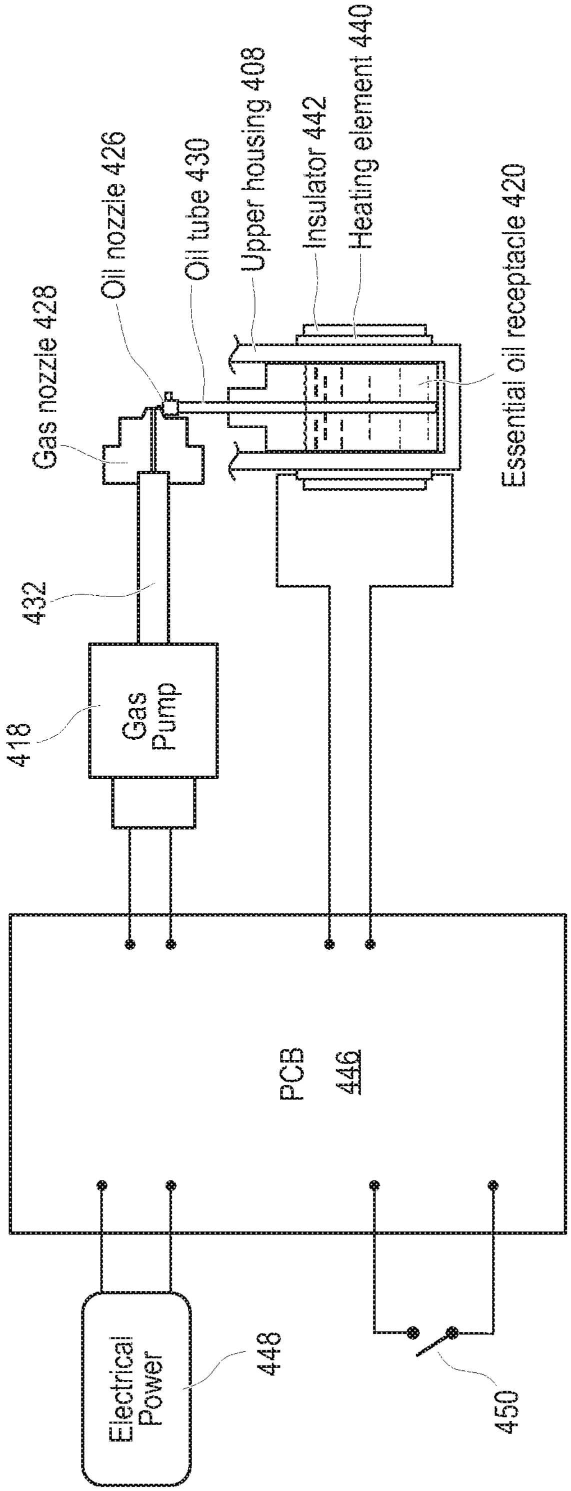
FIG. 7 is a diagrammatic view of some of the components of the atomizer of FIG. 6.

FIG. 7 shows a diagrammatic representation of components of the atomizer 400 of FIG. 6. The electronics unit 436 can include a printed circuit board 446 configured to be connected to an electrical power source/power source connection 448, the gas pump 418, and the heating element 440. The printed circuit board 446 can also be connected to switches or other user input devices 450 or mechanisms. The printed circuit board 446 can therefore be in electrical communication with the electrical power source/power source connection 448, user input devices 450, the pump 418, and the heating element 440. The printed circuit board 446 can comprise control circuitry configured to send or receive electrical signals to each of the components that are in electrical communication with the printed circuit board 446 and can thereby manage and control power provided to the pump 418 or heating element 440. FIG. 7 also diagrammatically shows the insulator 442, the oil receptacle 420 the upper housing 408, the oil tube 430, the oil nozzle 426, the gas nozzle 428, and the gas tube 432. The heating element 440 can apply heat to the receptacle 420 or to the upper housing 408 via conduction.

Figure 8:
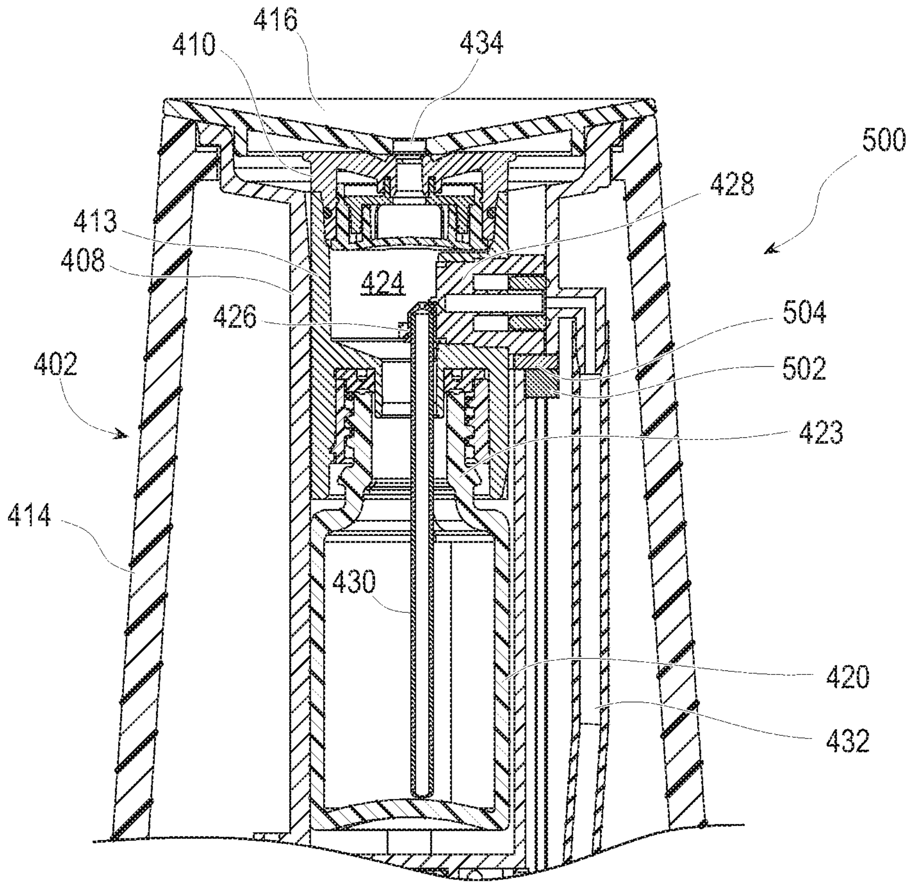
FIG. 8 is a side section view of an upper end of an essential oil atomizer of the present disclosure.

FIG. 8 shows an embodiment of an atomizer 500 having many components duplicated from atomizer 400 and which performs similar functions as in atomizer 400 and are therefore indicated with the same numerals used in connection with atomizer 400 in FIGS. 6 and 7. Only an upper end of the atomizer 500 is shown in side view cross-section in FIG. 8 to show detail at the atomization housing 413 and atomization chamber 424.

The atomizer 500 can comprise a heating element 502 electrically connected with the electronics unit 436 in a manner similar to heating element 440. Thus, the electronics unit 436 can electrically generate heat with the heating element 502. The heating element 502 can be mounted to the upper housing 408 on a radially internal side of the heating element 502 and can be mounted to the bottom of a thermal block 504. The thermal block 504 can be configured to contact the gas nozzle 428 (or, in some embodiments, the oil nozzle 426, oil receptacle 420, oil tube 430, gas tube 432, or atomizer housing 412) when the atomizer 500 is fully assembled.

The heating element 502 can comprise a resistive heating element or another type of electrical heat generator described above in connection with heating element 440. The thermal block 504 can comprise a material having high heat transfer conductivity, such as metal or ceramic. The gas nozzle 428 can also comprise a material having high heat transfer conductivity, such as metal or ceramic. In this manner, the heating element 502 can generate heat is transferred via conduction to the thermal block 504 and transferred via conduction to the gas nozzle 428. This heat can increase the departure of the gas nozzle 428 so that gas flowing through the gas tube 432 is heated as it passes through the gas nozzle 428. That heated gas can then come into contact with oil at the top of the oil nozzle 426, heat the oil at that point, and thereby thin or start to evaporate the oil to improve atomization and droplet formation of the oil within the atomization chamber 424.

In some embodiments, the oil nozzle 426 can be formed with, contacting, or attached to the gas nozzle 428. Therefore, the oil nozzle 426 can have its temperature increased by heat transferred via the gas nozzle 428. Raising the temperature of the oil nozzle 426 can consequently increase the temperature of oil at the outlet of the oil nozzle 426 even further, thereby improving atomization and droplet formation even further.

The heating element 502 and thermal block 504 can be beneficially implemented where space within the atomizer 500 is limited or where high electrical heating efficiency is desired. The heating element 502 can be significantly smaller in size than a heating element (e.g., 440) that must extend along a significant portion of the oil receptacle 420. The heating element 502 can also be beneficial in environments where the gas or oil does not need to be heated a large amount, and a small heating element 502 can therefore suffice to ensure proper oil heating at the atomization chamber 424. Heating the gas nozzle 428 and oil nozzle 426 can also help to prevent oil residue buildup on the nozzles and within the atomization chamber 424 by thinning oil or melting residue on the nozzles.

Figure 9:
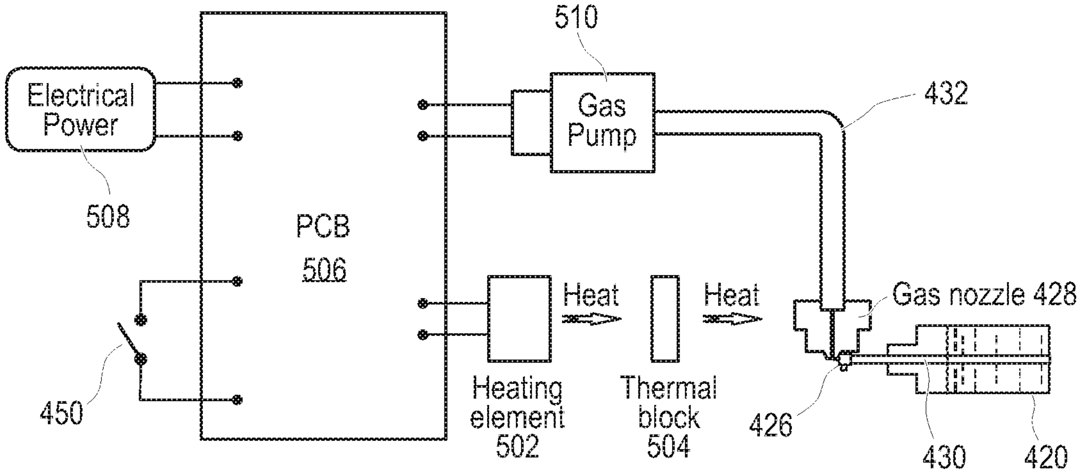
FIG. 9 is a diagrammatic view of some of the components of the atomizer of FIG. 8.

FIG. 9 is a diagrammatic view of components of the atomizer 500. In this embodiment, a printed circuit board 506 can be connected to an electrical power source/power source connection 508, a gas pump 510, user input device 450, and a heating element 502. As indicated in FIG. 9, the printed circuit board 506 can generate heat at the heating element 502 that is transferred to the thermal block 504 and then, in turn, to the gas nozzle 428.

Figure 10:
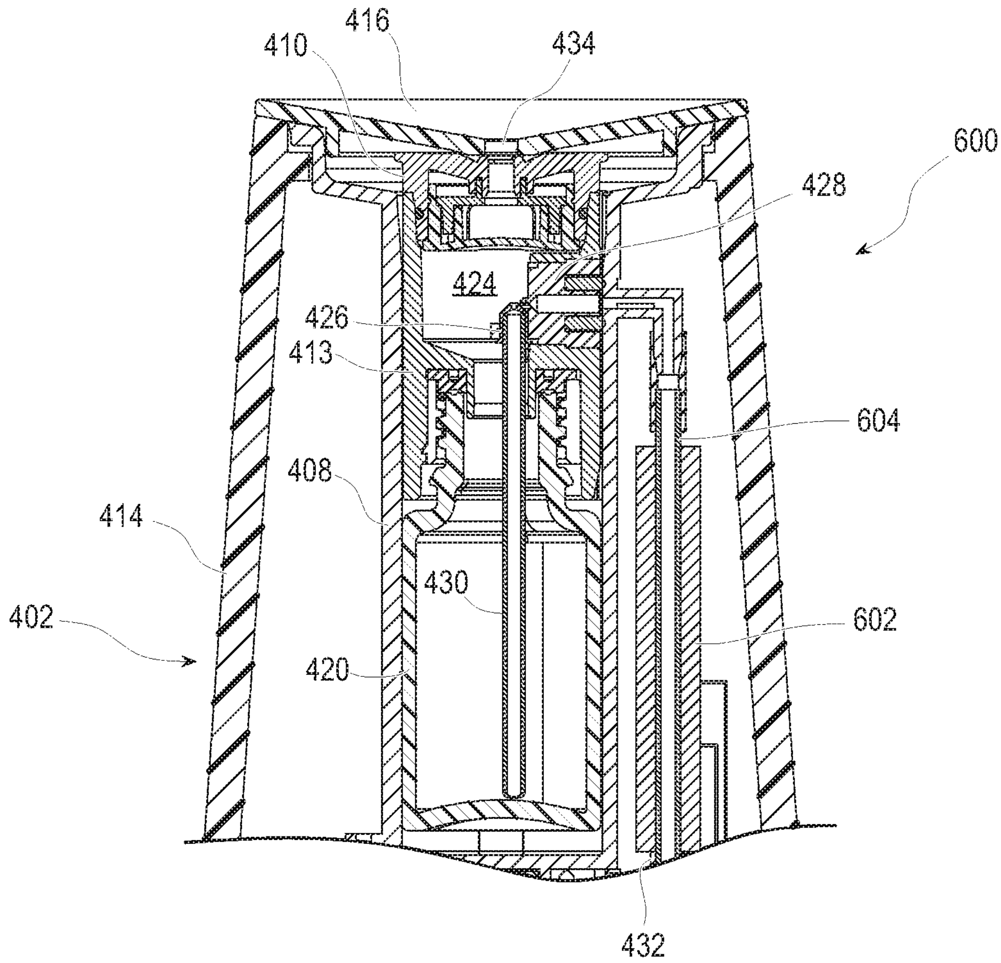
FIG. 10 is a side section view of an upper end of an essential oil atomizer of the present disclosure.
Figure 11:
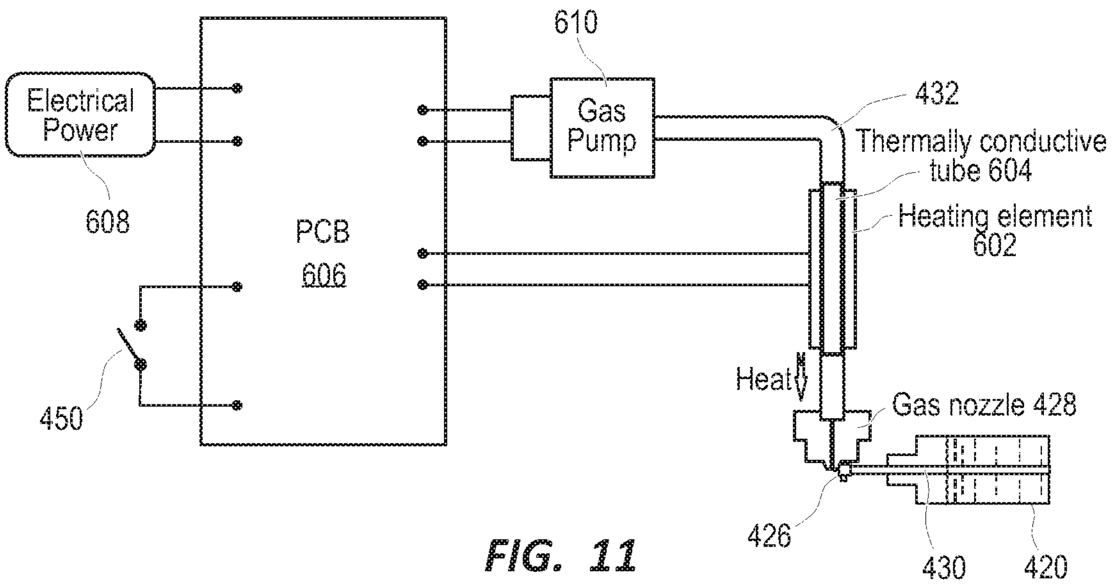
FIG. 11 is a diagrammatic view of some of the components of the atomizer of FIG. 10.

FIG. 10 shows an embodiment of an atomizer 600 having many components duplicated from atomizer 400 and which perform similar functions as their counterparts in atomizer 400 and are therefore indicated with the same numerals in FIGS. 10 and 11 as used in connection with atomizer 400. Only an upper end of the atomizer 600 is shown in side view cross-section in FIG. 10 to show detail at the upper end of the gas tube 432.

The atomizer 600 can comprise a heating element 602 electrically connected with the electronics unit 436 in a manner similar to heating element 440. Thus, the electronics unit 436 can electrically generate heat with the heating element 602. The heating element 602 can be mounted to a thermally conductive tube 604 that is connected to the gas tube 432 and that extends through the heating element 602. The thermally conductive tube 604 can be in fluid communication with an inlet side of the gas nozzle 428 when the atomizer 600 is fully assembled.

The thermally conductive tube 604 can beneficially comprise a material with high thermal conductivity, such as a metal or ceramic material, but in some embodiments, other types of less thermally conductive material can be used such as, for example, polymers or rubber. Thus, the tube can be described as being “thermally conductive” because it is used to conduct heat from the heating element 602 to elevate the temperature of gas within the tube 604. In other words, gas flowing through the thermally conductive tube 604 can be heated due to the thermally conductive tube 604 having an elevated temperature caused by heat generated in the heating element 602 external to the tube 604. In some embodiments, the gas tube 432 can extend through the heating element 602 instead of connecting to a separate thermally conductive tube 604 that extends through the heating element 602.

The heating element 602 can comprise a resistive heating element or another type of electrical heat generator described above in connection with heating element 440. The thermally conductive tube 604 can comprise a material having high heat transfer conductivity, such as metal or ceramic. In this manner, the heating element 602 can generate heat that is transferred via conduction to the thermally conductive tube 604 to heat the tube 604 and the gas positioned in or flowing through it. This heat can increase the temperature of the gas entering the gas nozzle 428. Thus, gas flowing through the gas tube 432 can be heated before it enters the gas nozzle 428. That heated gas can then come into contact with oil at the top of the oil nozzle 426, heat the oil at that point, and thereby improve atomization and droplet formation of the oil within the atomization chamber 424.

The heating element 602 and thermally conductive tube 604 can be beneficially implemented where space within the atomizer 500 is limited or where high electrical heating efficiency is desired. The heating element 602 can be smaller in size than a heating element (e.g., 440) that extends along a significant portion of the oil receptacle 420. The heating element 602 can also be beneficial in environments where the gas or oil does not need to be heated a large amount, and a small heating element 602 can therefore suffice to ensure proper oil heating at the atomization chamber 424. The heating element 602 can also be more easily removed or serviced within the atomizer 600 by removing the gas tube 432 and/or thermally conductive tube 604. Additionally, the amount of surface area within the thermally conductive tube 604 that is heated by the heating element 602 can be designed to ensure that the gas flowing through the tube 604 quickly rises to a desired temperature before it reaches the gas nozzle 428. In some embodiments, the gas flowing through the thermally conductive tube 604 can help reduce or eliminate the need for an insulator external to the heating element 602 because the gas flow can help wick away heat from the heating element 602 (e.g., via a convection process) and can thereby limit or prevent overheating in the thermally conductive tube 604. In some embodiments, insulation can be positioned around the heating element 602 to improve efficiency of the heat transfer from the heating element 602 into the tube 604. Additionally, in some embodiments, the heating element 602 can be positioned within the thermally conductive tube 604. See also FIGS. 12-13.

FIG. 11 shows a diagrammatic view of components of the atomizer 600 including a printed circuit board 606, electrical power source/power source connection 608, gas pump 610, heating element 602, gas nozzle 428, oil nozzle 426, oil tube 430, and oil receptacle 420. As indicated in FIG. 11, the printed circuit board 606 can be in electrical communication with the electrical power source/power source connection 608, the gas pump 610, and the heating element 602. Heat generated by the heating element 602 can be transferred through the thermally conductive tube 604 to gas flowing through it, and that heated gas can pass into the gas nozzle 428 to heat oil at the outlet of the oil nozzle 426 as the oil is atomized.

Figure 12:
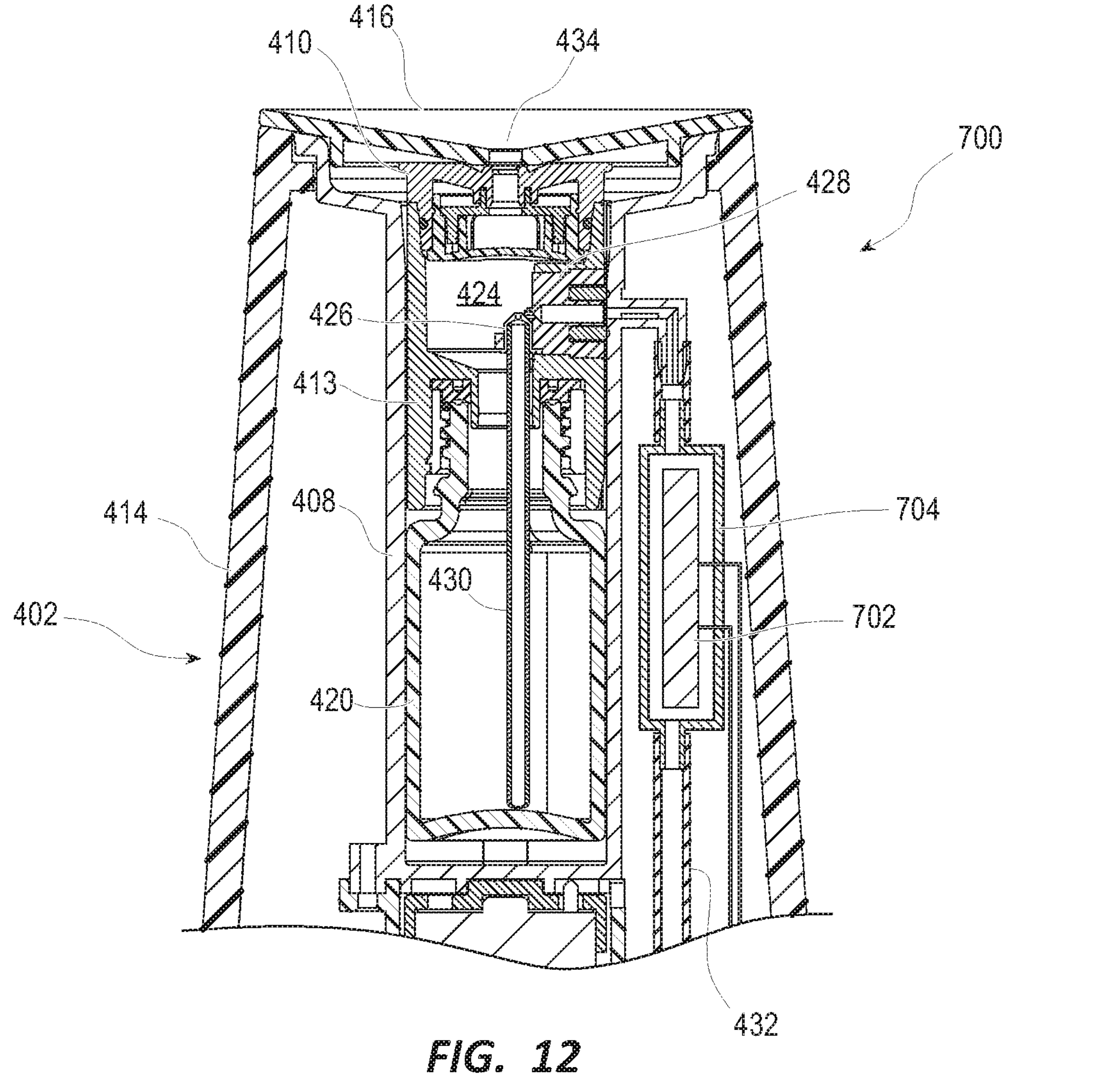
FIG. 12 is a side section view of an upper end of an essential oil atomizer of the present disclosure.
Figure 13:
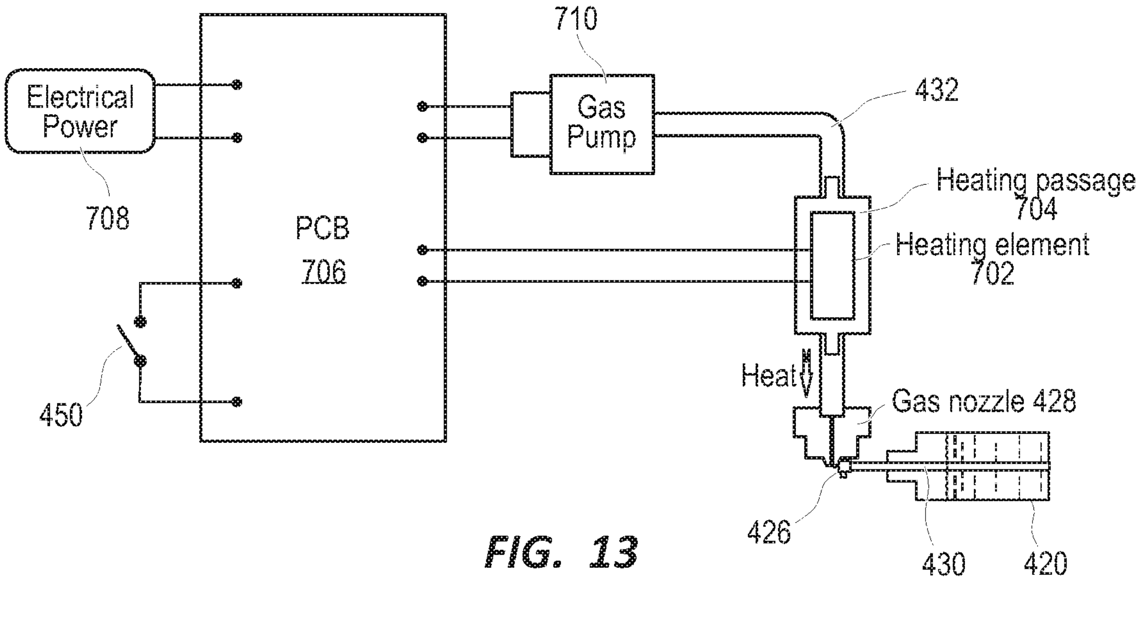
FIG. 13 is a diagrammatic view of some of the components of the atomizer of FIG. 12.

FIG. 12 shows an embodiment of an atomizer 700 having many components duplicated from atomizer 400 and which perform similar functions to atomizer 400 and are therefore indicated with the same numerals in FIGS. 12 and 13 as used in connection with atomizer 400. Only an upper end of the atomizer 700 is shown in side view cross-section in FIG. 12 to show detail at the upper end of the gas tube 432.

The atomizer 700 can comprise a heating element 702 electrically connected (e.g., by wires) with the electronics unit 436 in a manner similar to heating element 440. Thus, the electronics unit 436 can electrically generate heat with the heating element 702. The heating element 702 can be mounted to a heating passage 704 that is connected to the gas tube 432. The heating passage 704 can be in fluid communication with an inlet side of the gas nozzle 428 when the atomizer 700 is fully assembled, and gas flowing from the pump can pass into the gas tube 432, through the heating passage 704, and into the gas nozzle 428. The heating passage 704 can in some embodiments beneficially comprise a material with low thermal conductivity, such as an insulating material (e.g., rubber, fiberglass, polymer, or another insulator identified herein). Gas flowing through the heating passage 704 can be heated due to the heating element 702 generating heat and having an elevated temperature. In some embodiments, the heating element 702 can be positioned inside the gas tube 432 or within the gas tube 432 and within the heating passage 704. In some embodiments, the heating element 702 can be positioned at least partially within the gas nozzle 428.

The heating element 702 can comprise a resistive heating element or another type of electrical heat generator described above in connection with heating element 440. The heating passage 704 can comprise a material having low heat transfer conductivity. In this manner, the heating element 702 can generate heat that is transferred via conduction and convection to gas passing through heating passage 704. This heat can increase the temperature of the gas entering the gas nozzle 428. Thus, gas flowing through the heating passage 704 can be heated before it enters the gas nozzle 428. That heated gas can then come into contact with oil at the top of the oil nozzle 426, heat the oil at that point, and thereby improve atomization and droplet formation of the oil within the atomization chamber 424.

The heating element 702 and heating passage 704 can be beneficially implemented where space within the atomizer 700 is limited or where high electrical heating efficiency is desired. The heating element 702 can be smaller in size than a heating element (e.g., 440) that extends along a significant portion of the oil receptacle 420. The heating element 702 can also be beneficial in environments where the gas or oil does not need to be heated a large amount, and a small heating element 702 can therefore suffice to ensure proper oil heating at the atomization chamber 424. The heating element 702 can also be more easily removed or serviced within the atomizer 700 by removing the gas tube 432 and/or heating passage 704. Additionally, the amount of surface area of the heating element 702 can be designed to ensure that the gas flowing through the heating passage 704 quickly rises to a desired temperature before it reaches the gas nozzle 428 while also using the smallest heating element 702 needed in that setting.

In some embodiments, the gas flowing through the heating passage 704 can help reduce or eliminate the need for an insulator external to the heating passage 704 because the gas flow can help wick away heat from the heating element 702 (e.g., via convection) and thereby limit or prevent overheating in the heating passage 704. In some embodiments, insulation is positioned around the heating passage 704 to reduce heat loss through the heating passage 704.

FIG. 13 shows a diagrammatic view of components of the atomizer 700 including a printed circuit board 706, electrical power source/power source connection 708, gas pump 710, heating element 702, gas nozzle 428, oil nozzle 426, user input device 450, or oil tube 430, and oil receptacle 420. As indicated in FIG. 13, the printed circuit board 706 can be in electrical communication with the electrical power source/power source connection 708, the gas pump 710, and the heating element 702. Heat generated by the heating element 702 can be transferred through the heating passage 704 to gas flowing through it, and that heated gas can pass into the gas nozzle 428 to heat oil at the outlet of the oil nozzle 426 as the oil is atomized.

The embodiments disclosed herein also relate to methods for atomizing essential oil. An example method includes generating gas flow through a gas nozzle, generating oil flow through an oil nozzle, wherein the gas flow passes over an outlet of the oil nozzle to atomize the oil flow, and raising a temperature of the oil flow to increase atomization of the oil flow as the gas flow passes over the outlet. Generating gas flow through the gas nozzle can comprise using a pump (e.g., 418) or similar airflow generator to force air through a gas nozzle (e.g., 428). The gas nozzle can comprise a narrowed end outlet configured to accelerate and direct the gas stream passing through the gas nozzle so that the airflow passes across the outlet of the oil nozzle (e.g., 426). The passage of gas flow over the oil nozzle can generate a low pressure region above the oil nozzle to draw oil through the nozzle from a reservoir or receptacle (e.g., 420) in fluid communication with the oil nozzle (e.g., via 430). The oil flow can be atomized when subjected to the moving gas flow, and the droplets of oil can be carried by the gas flow from the atomizer.

Raising the temperature of the oil flow to increase atomization of the oil flow (as compared to the rate of atomization of the oil flow without the temperature being raised) can comprise heating the oil before it reaches the oil nozzle so that the oil has a higher than usual temperature (e.g., an elevated temperature relative to conventional room temperature, within a range of about 35 degrees Celsius to about 40 degrees Celsius, etc.) when it comes into contact with and is atomized by the gas flow. Raising the temperature of the oil flow to increase atomization of the oil flow can also comprise applying heat to the oil flow by raising the temperature of the gas flow. In other words, the gas flow can be heated, and the heat in the gas flow can be transferred to the oil as the gas flow passes over the oil nozzle, thereby heating the oil flow via the heated gas flow.

Furthermore, raising the temperature of the oil flow to increase atomization of the oil flow can comprise raising the temperature of parts or components of the atomizer, such as by applying heat to the oil nozzle or gas nozzle, to the oil receptacle, or to a housing of the atomizer. In this manner, heat can be transferred from a heater to the oil or gas indirectly through the components of the atomizer. Raising the temperature can therefore include positioning and powering a heater in the atomizer. Additional embodiments and variations of these methods will be apparent to those having ordinary skill in the art and with the benefit of the present disclosure.

Figure 14:
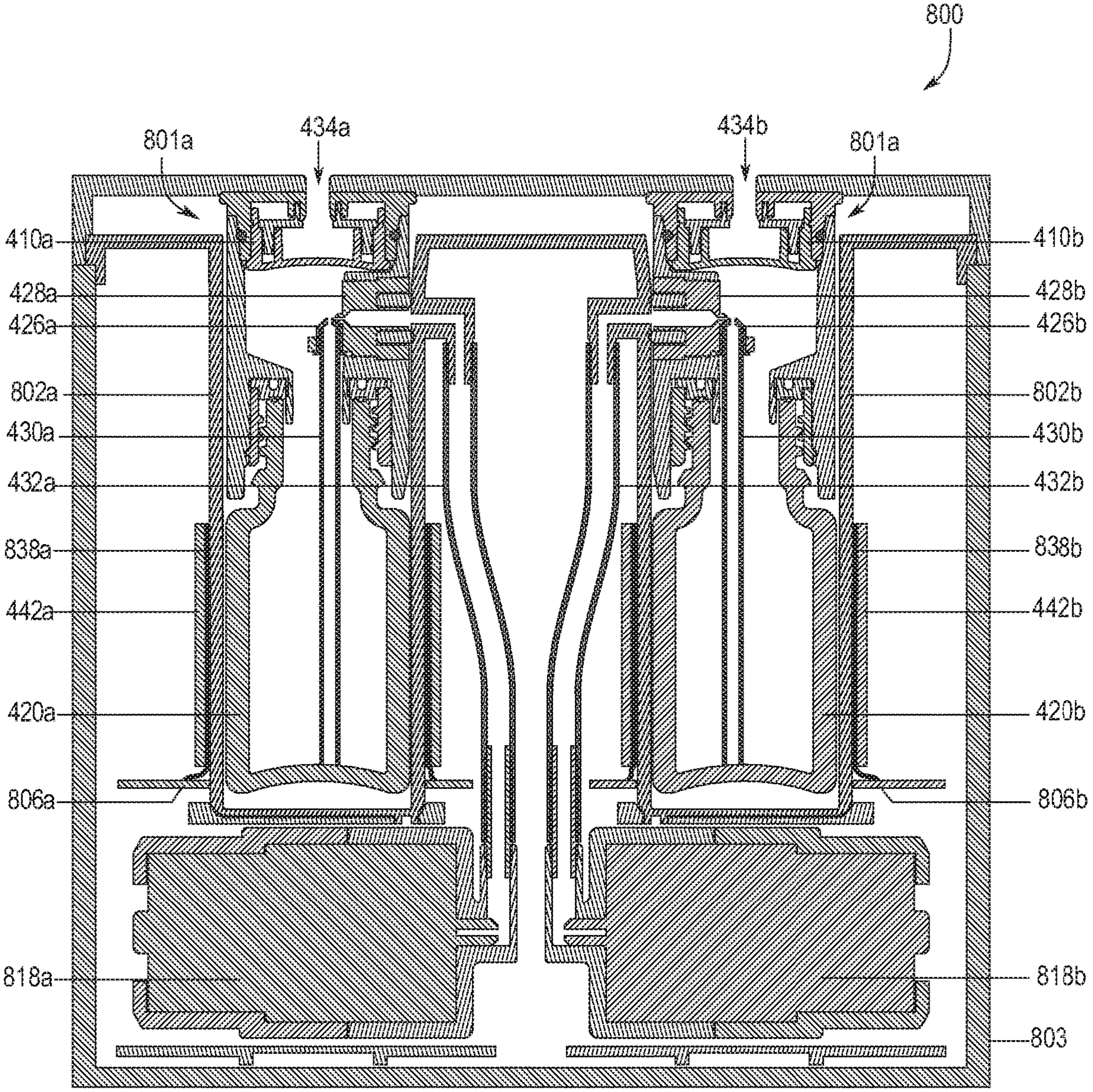
FIG. 14 is a cross-sectional side view of an essential oil atomizer of the present disclosure.

FIG. 14 shows an example embodiment of a multi-diffuser atomizer 800 having multiple diffusers 801*a*, 801*b* (collectively 801). The diffusers 801 can be comparable to, and include some or all of the features of, any of the atomizers discussed herein. For instance, many components of diffusers 801 are duplicated from atomizer 400 and therefore share common reference numerals. It will be understood that the letters "a" and "b" have been added to select reference numbers differentiate between the components of diffuser 801*a* and diffuser 801*b*. The parts and features of this essential oil atomizer 800 can have similar functions and can perform similar effects as their corresponding parts described in previous embodiments shown above. In some embodiments, the multi-diffuser atomizer 800 is symmetric across a central vertical axis extending through the multi-diffuser atomizer 800.

The atomizer 800 can comprise a first chassis 802*a* configured to retain a first diffuser 801*a* and a second chassis 802*b* configured to retain a second diffuser 801*b*. In some embodiments, a single chassis can be configured to retain multiple diffusers 801. For example, the first and second chassis 802 can be formed as a single piece or part of the single housing 803.

In some embodiments, the multi-diffuser atomizer 800 can include multiple pumps 818*a*, 818*b* (collectively 818). The pumps 818 (i.e., gas or air pumps, air or gas compressors, or similar air flow providers) can be located within the housing 803, below respective diffusers 801. In some embodiments, a first pump 818*a* is configured to provide gas flow to the first diffuser 801*a*, and a second pump 818*b* is configured to provide gas flow to the second diffuser 801*b*.

In some embodiments, the multi-diffuser atomizer 800 includes a single pump configured to provide gas flow to each of the diffusers 801. For instance, gas tubes 432*a*, 432*b* can receive output (i.e., gas flow) from a common pump (not shown in FIG. 14). The gas tubes 432*a* and 432*b* can be coupled with valves (not shown) such that the valves can control gas flow independently to each diffuser 801 while sharing a common pump.

Similar to previous embodiments, the multi-diffuser atomizer 800 can include an electronics units 806*a*, 806*b* (collectively 806) (e.g., a printed circuit board (PCB), power electronics, buttons, connectors, etc.). In some embodiments, each diffuser 801 comprises its own electronics unit 806 to be in electrical communication with the respective pumps 818. In other words, a first electronics unit 806*a* can be operatively coupled with the first diffuser 801*a*, and a second electronics unit 806*b* can be operatively coupled with the second diffuser 801*b* such that the electronics units can control the operation of the diffusers 801 independently. In some embodiments, each diffuser 801 is operatively coupled with a single electronics unit.

The diffusers 801 can further include heaters 838*a*, 838*b* (collectively 838) The heaters 838 can be substantially similar to heater 438 with reference to FIGS. 6 and 7. As used herein, multiple heaters in an atomizer can be referred to as a heating assembly. The heaters 838 can substantially surround their respective oil receptacles 420. The heaters 838 can be positioned on a radially external side of the oil receptacles 420 relative to a central axis of the diffusers 801. The heat generated by the heaters 838 can be transferred (e.g., via conduction, radiation, and convection) to and through the walls of the oil receptacles 420, and into oil within the oil receptacles 420, thereby heating and raising the internal temperature of oil in the oil receptacles 420. The heaters 838 can also include insulators 442*a*, 442*b* (collectively 442) externally radially surrounding the oil receptacles 420. The insulators 442 can help improve efficiency of the heaters 838 by limiting heat transfer in a radially outward direction from the oil receptacles 420. The insulators 442 can comprise a thermally insulating material such as fiberglass, foam rubber, ethylene vinyl acetate (EVA) foam, urethane foam, cork, polystyrene foam, cellulose, similar materials, and combinations thereof.

The heaters 838 can have a length dimension that is substantially equal to an overall length/height dimension of the respective oil receptacles 420. In this manner, the heaters 838 can apply heat along the overall length of the oil receptacles 420 and thereby ensure that substantially all of the oil in the receptacles 420 is heated by the heaters 838.

In some embodiments, the heaters 838 can extend along less than the entire length of the oil receptacles 420, such as, for example, along half of the length of the receptacles 420 or less. In some embodiments, the heaters 838 can extend along only an upper end of the receptacles 420 to heat the oil just before it enters the oil nozzles 426. In some embodiments, the heaters 838 can extend along only the lower end of the receptacles 420. This can be beneficial to apply heat to oil that accumulates at the bottom of the receptacles 420 and to allow the oil to start to cool as it moves up the oil tubes 430 before being atomized at the oil nozzles 426.

In some embodiments, the heaters 838 can be positioned beneath the oil receptacles 420 and can therefore apply heat to the bottom of the oil receptacles 420. The size of the heaters 838 can be configured to apply sufficient heat to the oil to raise its temperature to a range such as about 30 degrees Celsius to about 40 degrees Celsius at the oil nozzles 426.

In some embodiments, a single heater (not shown in FIG. 14) can be configured to heat both oil receptacles 420. A single heater can be configured to surround the oil receptacles 420. In some embodiments, the single heater can comprise a heating pad that is positioned below the oil receptacles 420.

The diffusers 801 can include vent openings 434*a*, 434*b* (collectively 434) configured to dispense atomized oil and gas. For example, when the atomized oil and gas flows toward the vent openings 434, it needs to pass through the filter housings 410, where the mixed airflow can be filtered to recycle larger essential oil droplets and reduce the waste of essential oils while the smaller essential oil droplets will pass through the filter housings 410 to be dispensed through the vent openings 434. In other words, the multi-diffuser atomizer 800 can include vent openings or spray outlets 434 through which the atomized oil and gas is configured to be expelled into the mixing chamber.

Similar to previous embodiments, one or more printed circuit boards (e.g., in electronics unit 806) can be in electrical communication with the electrical power source/power source connection, user input devices, the pump 818, and the heaters 838. The printed circuit boards can comprise control circuitry configured to send or receive electrical signals to each of the components that are in electrical communication with the printed circuit boards and can thereby manage and control power provided to the pumps 818 or heaters 838.

The diffusers 801 can be configured to operate independently or in combination with one another. In some embodiments, the diffusers 801 can share various components of the multi diffuser atomizer 800. For example, the diffusers 801 can share a common control circuit that can synch the on/off controls, temperature controls, gas output rates, etc. The diffusers 801 can also be powered by a common battery or other power source operatively coupled to a common printed circuit board. In some examples, the diffusers 801 can shared a common mist outlet and/or filter. As discussed above, the diffusers can share a common pump.

It will be appreciated that while the multi-diffuser atomizers discussed herein are depicted with two diffusers, any number of diffusers can be used. For instance, in some embodiments, the housing comprises a total of three or more diffusers. In such cases, the multiple diffusers can each comprise their own pump, chassis, oil receptacle, atomization housing, heaters, and other components associated with the diffusers 801 of FIG. 14. In some cases, a single heater can be provided in the housing 803 and can be configured to provide heat to multiple diffusers 801 or oil receptacles simultaneously. For example, a heater 838 can wrap around or otherwise surround multiple oil receptacles 420 to heat multiple supplies of oils in the atomizer 800.

Figure 15:
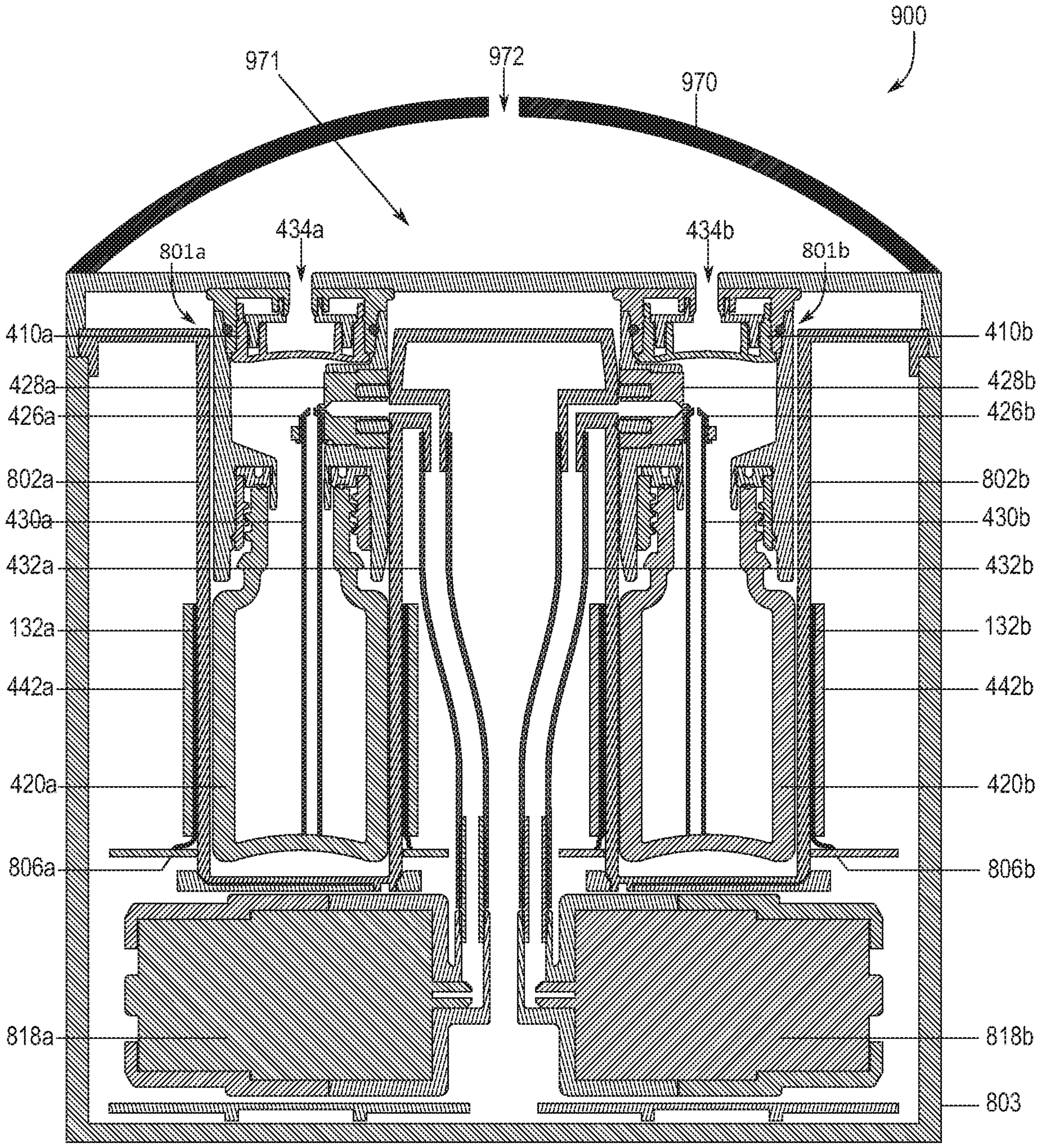
FIG. 15 is a cross-sectional side view of an essential oil atomizer of the present disclosure.

FIG. 15 shows an embodiment of a multi-diffuser atomizer 900. The multi-diffuser atomizer 900 can be comparable to, and include some or all of the features of any of the atomizers discussed herein. For instance, many components of multi-diffuser atomizer 900 are duplicated from multi-diffuser atomizer 800 and are therefore indicated with the same numerals in FIG. 15 as used in connection with multi-diffuser atomizer 800.

In some embodiments, the multi-diffuser atomizer 900 can include a cover or shell 970. The shell 970 can be positioned above the housing 803 and can be substantially dome-shaped. The shell 970, in combination with a top surface of the housing 803 can define a mixing chamber 971. The shell 970 can be configured to at least partially cover the vent openings 434 such that the atomized oil and gas that is dispensed from the vent openings 434 is expelled into the mixing chamber 971. The mixing chamber 971 can be configured to allow combining or intermingling of the atomized oil expelled from vent opening 434*a* and the atomized oil expelled from the vent opening 434*b*.

The shell 970 can further define an aperture or shell opening 972 configured to release the mixed atomized oil into the atmosphere. While only one shell opening 972 is shown, some embodiments may include multiple openings formed in the shell 970. The size of the shell opening 972 can depend on a desired expulsion rate. In some embodiments, the size of the shell opening 972 can be adjusted by a user. In some examples, the shell 970 can include a filter (not shown), similar to filter housings 410, to filter droplets of oil from the mixed atomized oil and gas in the mixing chamber 971. In some embodiments, the filter housings 410 are not positioned near the vent openings 434*a*, 434*b* and a single filter housing (not shown) is positioned in the dome opening 972 instead.

The shell 970 can be shaped and sized to encourage mixing or combining of the atomized oil and gas. For instance, the atomized oil and gas expelled from the vent openings 434*a*, 434*b* can create turbulence within the mixing chamber 971 to promote intermingling of the atomized oil and gas expelled from each vent opening 434. In some embodiments, the shell 970 can be used in combination with a mixing apparatus (such as a fan) configured to generate airflow within the mixing chamber 971 to promote increase intermingling of the atomized oils. It will be appreciated that the cover or shell 970 is not limited to a dome or curved shape. For example, the shell 970 can be substantially rectangular in shape, having flat walls, oval-shaped, box-shaped, tube-shaped, annular-shaped, etc.

In some embodiments, the shell 970 can be integrally formed with the housing 803. In some embodiments, the shell 970 can be attached to the housing 803. Any suitable attachment means can be implemented to secure the shell 970 to the housing 803, including adhesives, threads, snaps, fasteners, friction-fitting, etc. In some embodiments, the shell 970 can be removably attached to the housing.

Figure 16:
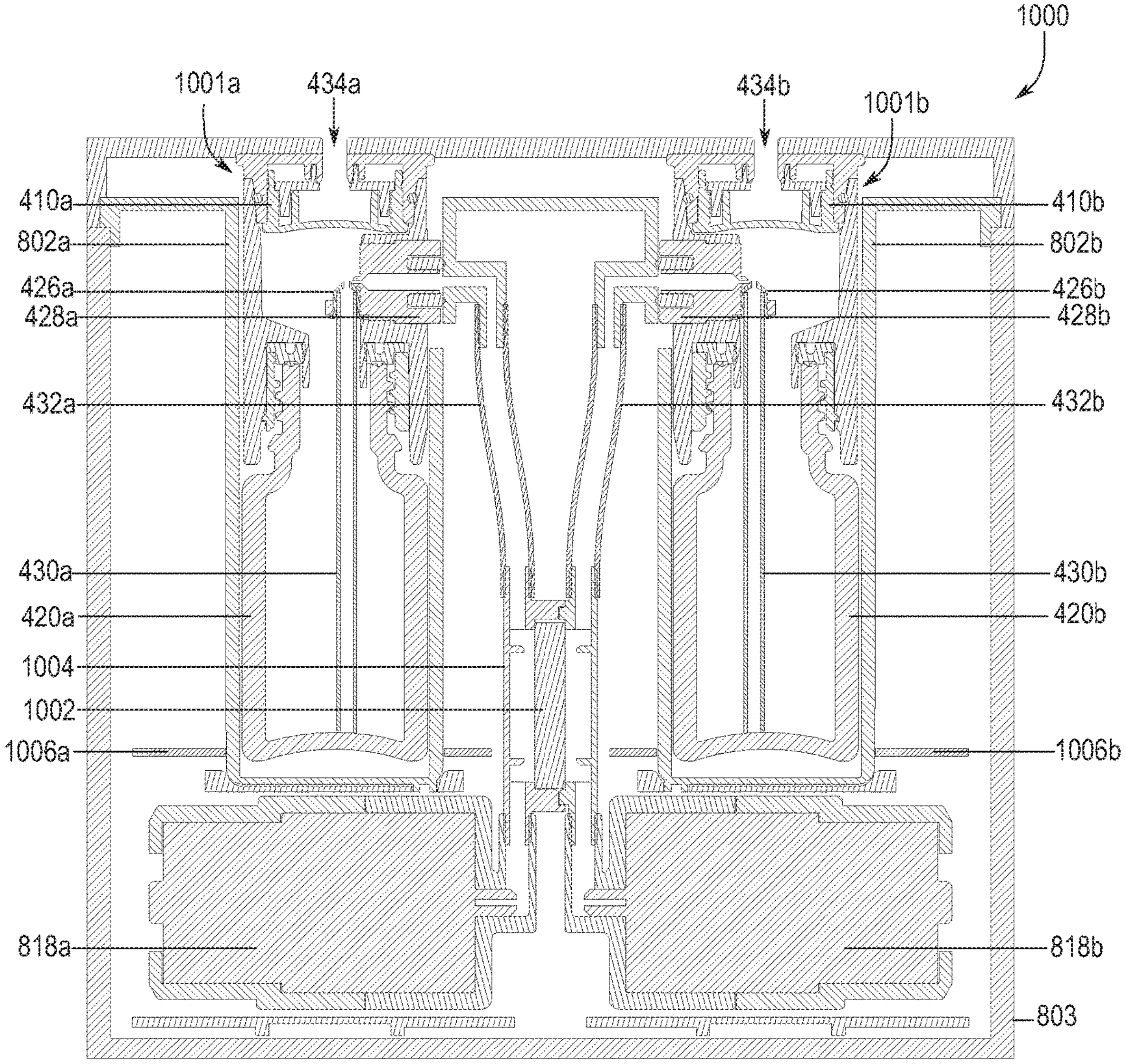
FIG. 16 is a cross-sectional side view of an essential oil atomizer of the present disclosure.

FIG. 16 shows an embodiment of a multi-diffuser atomizer 1000. The multi-diffuser atomizer 1000 can be comparable to any of the atomizers discussed herein. For instance, the multi-diffuser atomizer 1000 can have many components duplicated from atomizers 700 and 800 and which perform similar functions to atomizers 700 and 800 and are therefore indicated with similar numerals.

The multi-diffuser atomizer 1000 can comprise a heating element 1002 mounted to a heating passage 1004 that is connected to each of the gas tubes 432. The heating element 1002 and the heating passage 1004 can be substantially similar to the heating element 702 and heating passage 704, with the exception that the heating element 1002 and heating passage 1004 are configured for use with multiple diffusers 1001. The heating passage 1004 can be in fluid communication with an inlet side of the gas nozzles 428 when the multi-diffuser atomizer 1000 is fully assembled, and gas flowing from the pumps 818 can pass through the heating passage 1004 and into the gas tubes 432. The heating passage 1004 can, in some embodiments, beneficially comprise a material with low thermal conductivity, such as an insulating material (e.g., rubber, fiberglass, polymer, or another insulator identified herein). Gas flowing through the heating passage 1004 can be heated due to the heating element 1002 generating heat and having an elevated temperature. In some embodiments, the heating passage 1004 can be integrally formed with the gas tubes 432. In some embodiments, the heating passage 1004 is configured to be coupled with the gas tubes 432 on one end of the heating passage 1004 and attached to the pumps 818 at an opposite end of the heating passage 1004. In some embodiments, the heating element 1002 can be positioned at least partially within the gas nozzles 428. In some embodiments, the gas tubes 432 remain isolated and independent from one another, despite sharing a common heating element 1002. In other words, the heating element 1002 and heating passage 1004 can be configured to form an airtight seal between gas tube 432*a* and gas tube 432*b*, and gas from one gas tube 432*a* is not commingled with gas from the other gas tube 432*b* even though they are both heated by a single heating element 1002 and within a single heating passage 1004. The heating passage 1004 can therefore comprise two independent airways that respectively link to the two gas tubes 432 without mixing the air in each independent airway.

The heating passage 1004 can comprise a material having low heat transfer conductivity. In this manner, the heating element 1002 can generate heat that is transferred via conduction and convection to gas passing through heating passage 1004. This heat can increase the temperature of the gas entering the gas nozzles 428. Thus, gas flowing through the heating passage 1004 can be heated before it enters the gas nozzles 428. That heated gas can then come into contact with oil at the top of the oil nozzles 426, heat the oil at that point, and thereby improve atomization and droplet formation of the oil.

The heating element 1002 and heating passage 1004 can be beneficially implemented where space within the multi-diffuser atomizer 1000 is limited or where high electrical heating efficiency is desired. For instance, the heating element 1002 and passage 1004 can be positioned at a central location within the housing 803 in order to limit heat loss to the exterior of the atomizer 100. In some embodiments, the heating element 1002 and passage 1004 can be positioned at the opposite end of the tubes 432 to heat the air immediately before it enters the nozzle assemblies and to thereby limit heat loss. In some embodiments, the heating element 1002 and passage 1004 can be positioned in an insulating chamber or within insulation configured to reduce heat loss around the passage 1004.

In some embodiments, the gas flowing through the heating passage 1004 can help reduce or eliminate the need for an insulator external to the heating passage 1004 because the gas flow can help wick away heat from the heating element 1002 (e.g., via convection) and thereby limit or prevent overheating in the heating passage 1004. In some embodiments, insulation is positioned around the heating passage 1004 to reduce heat loss through the heating passage 1004.

Figure 17:
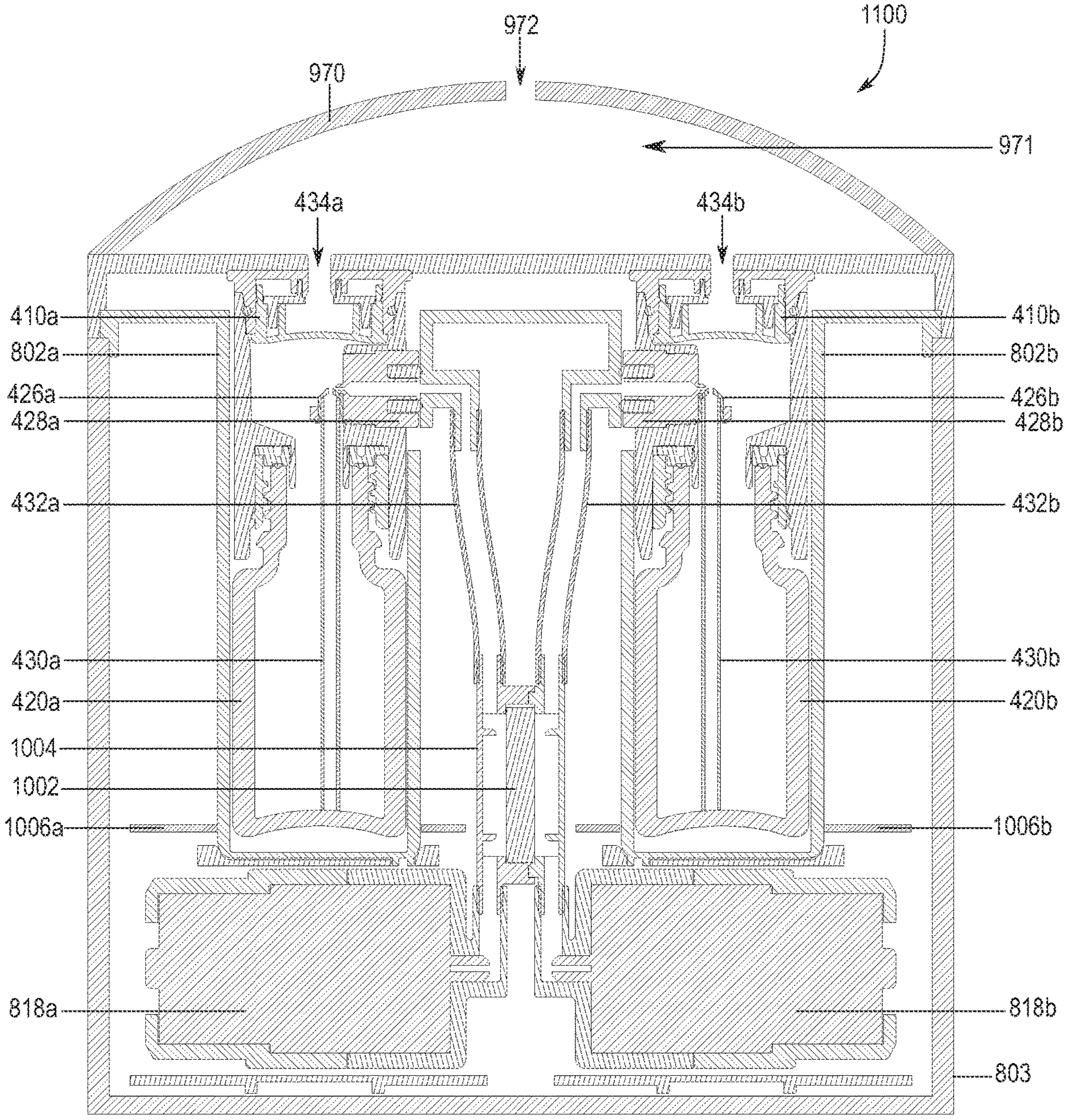
FIG. 17 is a cross-sectional side view of an essential oil atomizer of the present disclosure.

FIG. 17 shows an embodiment of a multi-diffuser atomizer 1100 including a shell 970. The multi-diffuser atomizer 1100 can be substantially similar to, and include some or all of the features of any of the atomizers discussed herein. For instance, many components of the multi-diffuser atomizer 1100 are duplicated from multi-diffuser atomizer 1000 and are therefore indicated with the same numerals. Further, the shell 970 can be substantially similar to, and include some or all of the features of the shell 970 on multi-diffuser atomizer 900 and are therefore indicated with the same numerals in FIG. 17 as used in connection with multi-diffuser atomizer 900.

Figure 18:
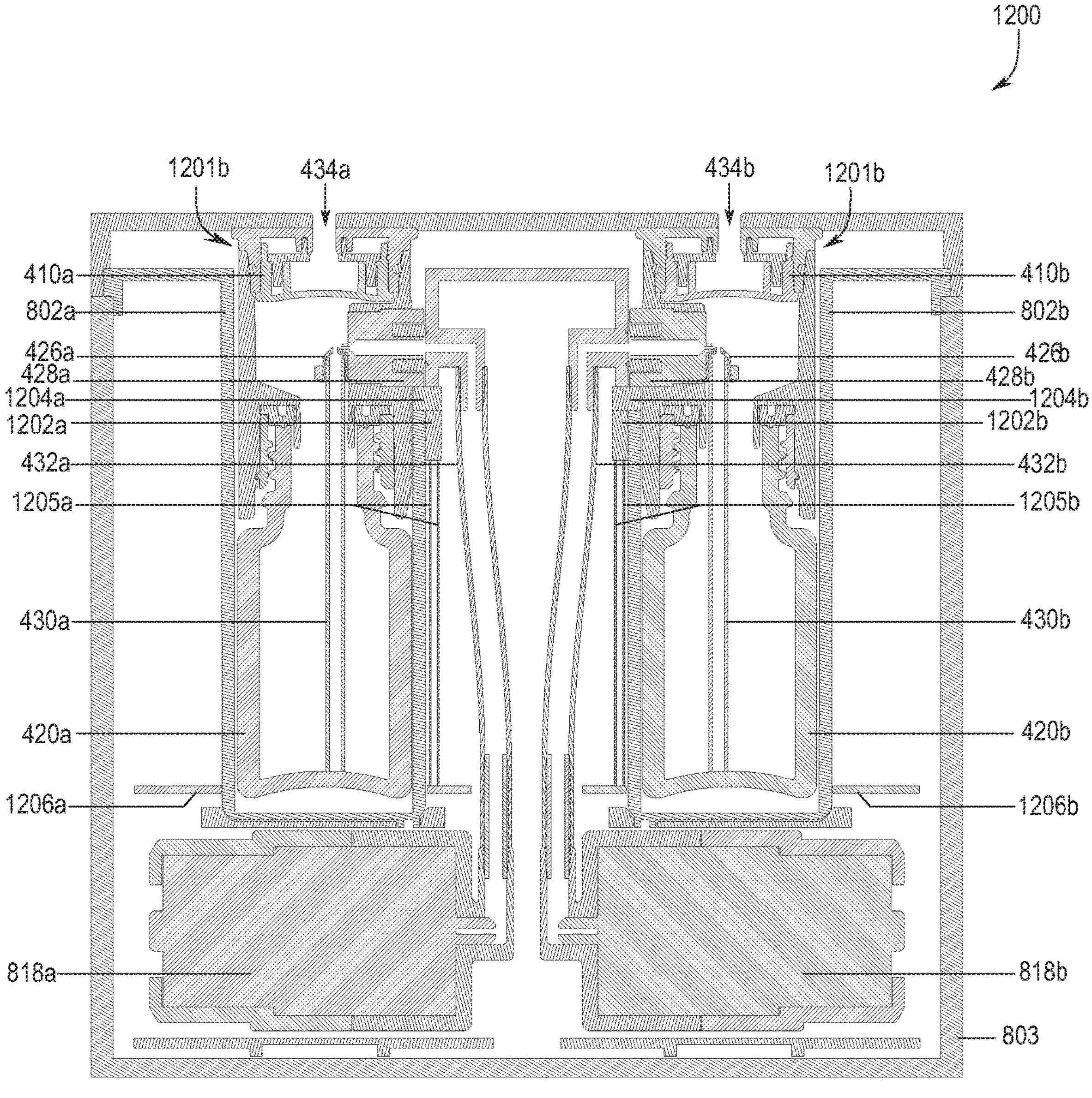
FIG. 18 is a cross-sectional side view of an essential oil atomizer of the present disclosure.

FIG. 18 shows an example embodiment of a multi-diffuser atomizer 1200 having multiple diffusers 1201*a*, 1201*b* (collectively 1201). The diffusers 1201 can be comparable to, and can include some or all of the features of, any of the atomizers discussed herein. For instance, many components of diffusers 1201 are duplicated from atomizer 500 and therefore share common reference numerals. It will be understood that the letters "a" and "b" at the end of a reference number has been added to differentiate between the components of diffuser 1201*a* from the components of diffuser 1201*b*. Further, the multi-diffuser atomizer 1200 can be substantially similar to the multi-diffuser atomizers discussed herein, such as multi-diffuser atomizers 800-1100.

The multi-diffuser atomizer 1200 can comprise a heating element 1202*a* in thermal communication with diffuser 1201*a*, and heating element 1202*b* in thermal communication with diffuser 1201*b*. The heating elements 1202*a*, 1202*b* (collectively 1202) can be mounted to the bottom of thermal blocks 1204*a*, 1204*b* (collectively 1204). The thermal blocks 1204 can be configured to contact the gas nozzles 428 (or, in some embodiments, the oil nozzles 426, oil receptacles 420, oil tubes 430, gas tubes 432, or atomizer housing 803) when the atomizer 1200 is fully assembled.

The heating elements 1202 can comprise a resistive heating element or another type of electrical heat generator described above in connection with heating element 440. The thermal blocks 1204 can comprise a material having high heat transfer conductivity, such as metal or ceramic. The gas nozzles 428 can also comprise a material having high heat transfer conductivity, such as metal or ceramic. In this manner, the heating element 1202 can generate heat is transferred via conduction to the thermal blocks 1204 and transferred via conduction to the gas nozzles 428. This heat can cause the gas flowing through the gas tubes 432 to be heated as it passes through the gas nozzles 428. That heated gas can then come into contact with oil at the top of the oil nozzles 426, heat the oil at that point, and thereby thin or start to evaporate the oil to improve atomization and droplet formation of the oil.

In some embodiments, the oil nozzles 426 can be formed with, contacting, or attached to the gas nozzles 428. Therefore, the oil nozzles 426 can have their temperature increased by heat transferred via the gas nozzles 428. Raising the temperature of the oil nozzles 426 can consequently increase the temperature of oil at the outlet of the oil nozzles 426 even further, thereby improving atomization and droplet formation even further.

The heating element 1202 and thermal blocks 1204 can be beneficially implemented where space within the atomizer 1200 is limited or where high electrical heating efficiency is desired. Similar to previous embodiments, a printed circuit board can generate heat at the heating elements 1202 via wires 1205*a*, 1205*b*. The heat generated at the heating elements 1202 can then be transferred to the thermal blocks 1204 and then, in turn, to the gas nozzles 428.

In addition to transferring heat from the heating elements 1202 to the gas nozzles 428, the thermal blocks 1204 can protect or shield the heating elements 1202 (e.g., during assembly/disassembly of the atomizer 1200).

The use of heaters, such as heaters 838, 1002, and 1202 discussed above can enable diffusion of thicker essential oils. In some embodiments, a single heating element 1202 can contact one or more thermal blocks 1204 connected to the diffusers 1201. Accordingly, although multiple heating elements 1202 and thermal blocks 1204 are shown in FIG. 18, it will be understood that a single heating element 1202 or single thermal block 1204 can be used to heat multiple gas nozzles and thereby heat multiple gas streams through the atomizer 1200.

Additionally, in some embodiments, the atomizer 1200 can comprise a combination of different types of heating apparatuses in a single housing 803. For instance, a first heating apparatus can be implemented in the atomizer 1200 with a heating element (e.g., 1202*a*) and a thermal block (e.g., 1204*a*) used to heat a gas nozzle (e.g., 428*a*), and a heating element (e.g., 838*b*) can be used to heat an oil receptacle (e.g., 420*b*) within the same housing 803. Similarly, mixed types of heating elements from other embodiments disclosed herein can be used in various embodiments of the present disclosure. In some cases, multiple heating apparatuses can be simultaneously or selectively used on a single diffuser (e.g., 1201*a*), such as a heating apparatus that heats the gas nozzle 428*a*, a heating apparatus that heats air in the gas line 432*a*, and a heating apparatus that heats the oil receptacle 420*a*. Having a variety of heating options on a single diffuser can make the diffuser more versatile in the types of oils that it can heat and distribute due to heating air, the oil receptacle, or the nozzle. Thus, the most efficient heating apparatuses can be used for each type of oil based on the oil's unique properties and the properties of the diffuser in which it is contained.

Figure 19:
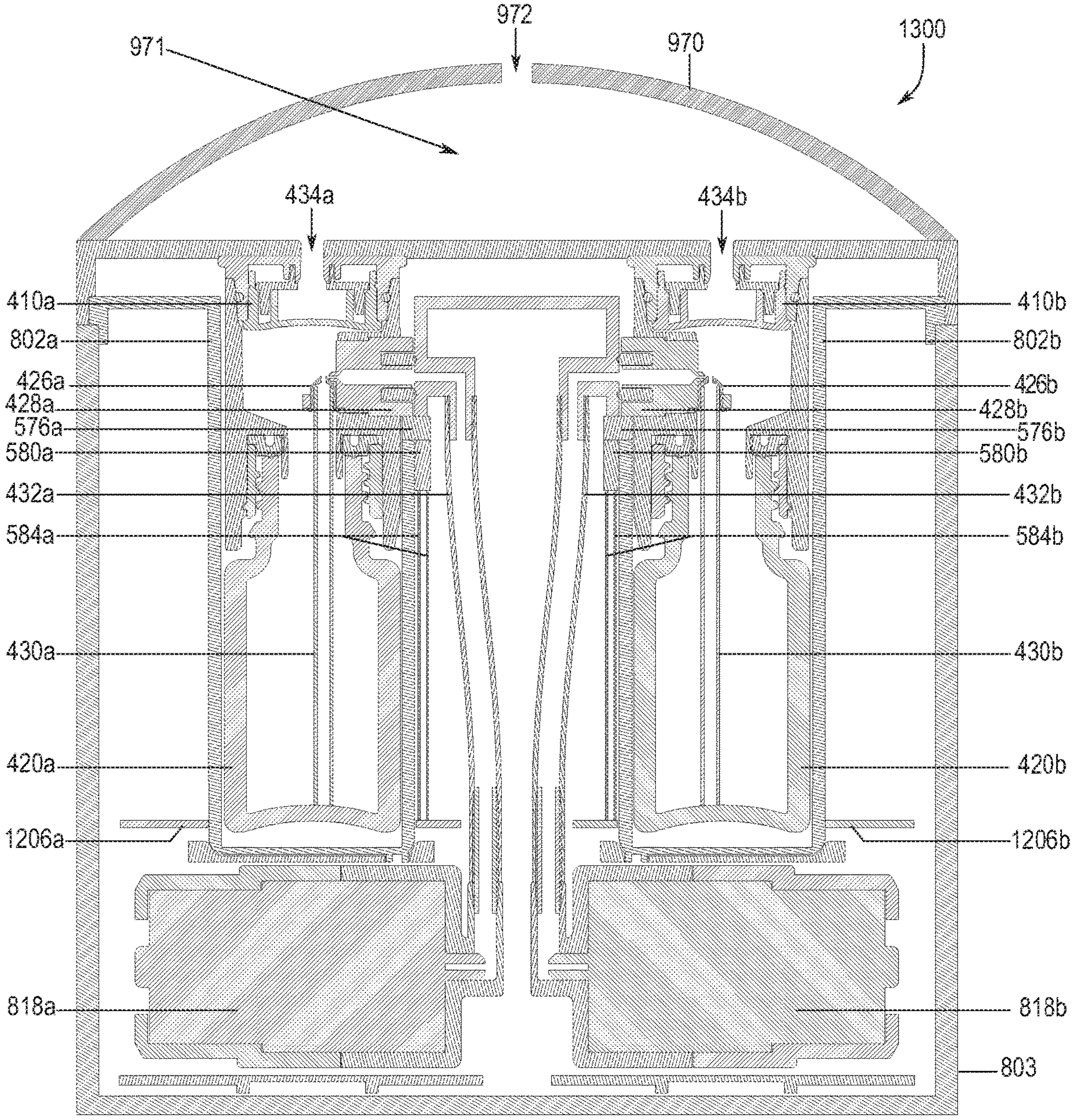
FIG. 19 is a cross-sectional side view of an essential oil atomizer of the present disclosure.

FIG. 19 shows an embodiment of a multi-diffuser atomizer 1300 including a shell 970. The multi-diffuser atomizer 1300 can be substantially similar to, and include some or all of the features of any of the atomizers discussed herein. For instance, many components of the multi-diffuser atomizer 1300 are duplicated from multi-diffuser atomizer 1200 and are therefore indicated with the same numerals. Further, the shell 970 can be substantially similar to, and include some or all of the features of the shell 970 on multi-diffuser atomizer 900 and are therefore indicated with the same numerals in FIG. 19 as used in connection with multi-diffuser atomizer 900.

Figure 20A:
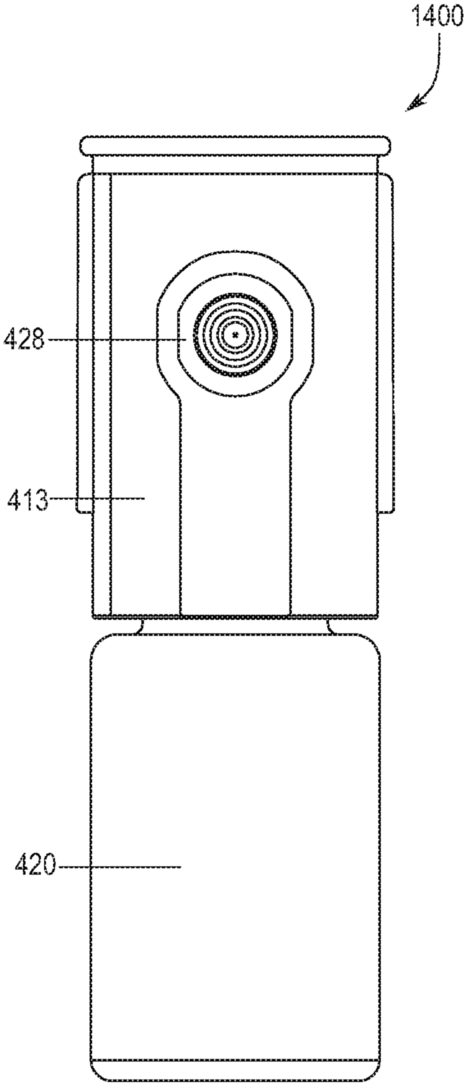
FIG. 20A is a side view of an oil diffuser of the present disclosure.
Figure 20B:
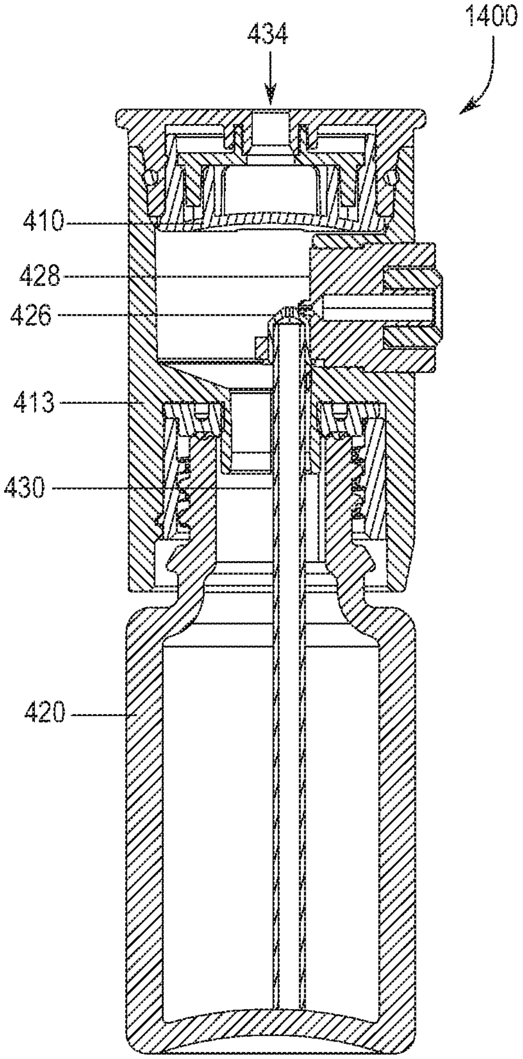
FIG. 20B is a cross-sectional side view of the oil diffuser of FIG. 20A.

FIG. 20A illustrates a modular diffuser 1400. Likewise, FIG. 20B illustrates a cross-sectional view of the modular diffuser 1400. The modular diffuser 1400 can be substantially similar to, and include some or all of the features of any of the atomizers/diffusers discussed herein. For instance, many components are duplicated and therefore share common reference numerals. In some embodiments, an atomizer or multi-diffuser atomizer as discussed herein can include one or more mounting location for mounting one or more oil diffusers within the housing. In some embodiments, the modular diffuser 1400 is a modular unit configured to be removable from the mounting location. For example, a top panel of the housing 803 in atomizers 800-1300 (through which the outlets 434 extend) can be removable in order to access and remove modular diffusers 1400 on each side of the housing 803. Further, a replacement diffuser can be configured to be connectable to the mounting location after removal of the modular diffuser 1400. The top panel can then be replaced to help keep the replacement modular diffuser retained in the housing 803.

In some embodiments, the replacement diffuser can have different properties relative to the modular diffuser 1400. For example, modular diffusers can vary in terms of oil capacity, diffusion rate, tube dimensions, nozzle dimensions, filtering capacity, and oil scent. The housing can comprise a total of three or more mounting locations for a total of three or more oil diffusers.

The present description provides examples, and is not limiting of the scope, applicability, or configuration set forth in the claims. Thus, it will be understood that changes may be made in the function and arrangement of elements discussed without departing from the spirit and scope of the disclosure, and various embodiments may omit, substitute, or add other procedures or components as appropriate. For instance, the methods described may be performed in an order different from that described, and various steps may be added, omitted, or combined. Also, features described with respect to certain embodiments may be combined in other embodiments.

Various inventions have been described herein with reference to certain specific embodiments and examples. However, they will be recognized by those skilled in the art that many variations are possible without departing from the scope and spirit of the inventions disclosed herein, in that those inventions set forth in the claims below are intended to cover all variations and modifications of the inventions disclosed without departing from the spirit of the inventions. The terms "including:" and "having" come as used in the specification and claims shall have the same meaning as the term "comprising."

What is claimed is:

1. An essential oil atomizer, comprising:
- a housing;
- a first oil diffuser and a second oil diffuser located within the housing, each of the first and second oil diffusers comprising:
  - an oil receptacle configured to store oil;
  - a gas line configured to provide gas; and
  - an atomizer nozzle assembly configured to diffuse oil and gas; and
- a heater in fluid communication with at least two independent airways of the gas lines, the heater configured to apply heat to the gas in the at least two independent airways.

2. The essential oil atomizer of claim 1, further comprising a first pump configured to provide gas to the first oil diffuser, and a second pump configured to provide gas to the second oil diffuser.

3. The essential oil atomizer of claim 1, wherein the heater comprises a first heating element configured to supply heat to the first oil diffuser, and a second heating element configured to supply heat to the second oil diffuser.

4. The essential oil atomizer of claim 3, wherein the first heating element and the second heating element are configured to heat the respective oil receptacles of the first and second oil diffusers.

5. The essential oil atomizer of claim 3, wherein the first heating element and the second heating element are configured to heat the respective atomizer nozzle assemblies of the first and second oil diffusers.

6. The essential oil atomizer of claim 1, wherein each atomizer nozzle assembly comprises an oil nozzle and a gas nozzle, wherein the heater is configured to apply heat to at least one gas nozzle of the first and second oil diffusers.

7. The essential oil atomizer of claim 1, wherein the heater is-positioned on an inlet side of the atomizer nozzle assemblies.

8. The essential oil atomizer of claim 1, further comprising a heating passage forming an airtight seal between the gas line of the first oil diffuser and the gas line of the second oil diffuser.

9. The essential oil atomizer of claim 1, wherein the atomized oil and gas from the first and second oil diffusers is expelled into a mixing chamber to form a mixture of atomized oil from the first and second oil diffusers.

10. The essential oil atomizer of claim 1, wherein the housing comprises a total of three or more oil diffusers.

11. An essential oil atomizer, comprising:

a housing connectable to a mixing shell, the mixing shell defining a mixing chamber and a shell outlet;

at least two oil diffusers connected to the housing, each of the at least two oil diffusers comprising:

an oil receptacle;

an atomizer nozzle assembly configured to atomize oil from the oil receptacle in a gas;

a gas line configured to provide the gas to the atomizer nozzle; and a spray outlet through which the atomized oil and gas is configured to be expelled into the mixing chamber; and a heating assembly configured to heat the gas within each gas line, the heating assembly comprising:

a heating passage that is connected to each of the gas lines; and a heater mounted in the heating passage;

wherein the atomized oil and gas from each of the at least two oil diffusers is configured to be combined in the mixing chamber and to be expelled through the shell outlet; and wherein flows through the gas lines of the at least two oil diffusers are configured to be isolated from each other from the heating passage to the atomizer nozzle assembly.

12. The essential oil atomizer of claim 11, wherein the heating assembly is configured to raise a temperature of the gas.

13. The essential oil atomizer of claim 12, wherein the heating assembly comprises a first heater configured to raise the temperature of a first oil diffuser of the at least two oil diffusers, and a second heater configured to raise the temperature of a second oil diffuser of the at least two oil diffusers.

14. The essential oil atomizer of claim 11, wherein the heating assembly is configured to heat gas on an inlet side of the atomizer nozzle assemblies.

15. The essential oil atomizer of claim 11, wherein the heating assembly is configured to raise the temperature of the oil by heating the oil before or while the oil flows to the nozzle assembly.

16. The essential oil atomizer of claim 15, wherein the heating assembly comprises a first heating element configured to at least partially surround one of the oil receptacles, and a second heating element configured to at least partially surround another of the oil receptacles.

17. An essential oil atomizer, comprising:

a housing having a first mounting location and a second mounting location;

first and second oil diffusers located within the housing, the first oil diffuser being positioned in the first mounting location, the second oil diffuser being positioned in the second mounting location, wherein the first and second oil diffusers are removable from the first and second mounting locations, each of the first and second oil diffusers comprising:

an oil receptacle;

a nozzle assembly in fluid communication with the oil receptacle, the nozzle assembly configured to atomize oil; and a gas line configured to provide gas to the nozzle assembly; and a heating element in fluid communication with each gas line of the first and second oil diffusers; and a heating passage forming an airtight seal between each gas line.

18. The essential oil atomizer of claim 17, further comprising a third oil diffuser, wherein the third oil diffuser is connectable to the housing in the first mounting location upon removal of the first oil diffuser from the first mounting location, the third oil diffuser having different properties relative to the first oil diffuser.

19. The essential oil atomizer of claim 17, wherein the nozzle assembly comprises an oil nozzle and a gas nozzle, wherein the oil nozzle is configured to be in fluid communication with the oil receptacle, and the gas nozzle is configured to expel the gas across the oil nozzle.

20. The essential oil atomizer of claim 17, wherein the housing comprises a total of three or more mounting locations for a total of three or more oil diffusers.

* * * * *